US010115319B2

(12) United States Patent
Walsh et al.

(10) Patent No.: US 10,115,319 B2
(45) Date of Patent: Oct. 30, 2018

(54) SYSTEMS AND METHODS FOR DETECTING OVERSTRIDING IN RUNNERS

(71) Applicant: President and Fellows of Harvard College, Cambridge, MA (US)

(72) Inventors: Conor J. Walsh, Cambridge, MA (US); Stephanie Hsiang-Ting Liu, Palo Alto, CA (US); Panagiotis Polygerinos, Gilbert, AZ (US); Daniel E. Lieberman, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 260 days.

(21) Appl. No.: 15/081,072

(22) Filed: Mar. 25, 2016

(65) Prior Publication Data

US 2016/0284231 A1    Sep. 29, 2016

Related U.S. Application Data

(60) Provisional application No. 62/138,809, filed on Mar. 26, 2015.

(51) Int. Cl.
*A63F 9/24* (2006.01)
*G09B 19/00* (2006.01)
(Continued)

(52) U.S. Cl.
CPC .......... *G09B 19/0038* (2013.01); *A61B 5/112* (2013.01); *A61B 5/1121* (2013.01);
(Continued)

(58) Field of Classification Search
None
See application file for complete search history.

(56) References Cited

U.S. PATENT DOCUMENTS 5,485,402 A    1/1996  Smith et al.
5,826,578 A *  10/1998 Curchod .............. A61B 5/1121
                                                          434/252
(Continued)

OTHER PUBLICATIONS

Laughton, C.A. et al., "Effect of Strike Pattern and Orthotic Intervention on Tibial Shock During Running," Journal of Applied Biomechanics, vol. 19, Issue 2, pp. 153-168, May 2003.
(Continued)

*Primary Examiner* — Paul A D'Agostino
(74) *Attorney, Agent, or Firm* — Greenberg Traurig, LLP; David J. Dykeman; Todd C. Basile

(57) ABSTRACT

Methods and systems for detecting overstride in runners include measuring, using an inertial measurement unit affixed to a shank of a person, an acceleration and an angle of the shank during a stride, monitoring, using a microprocessor, the shank acceleration measurements to detect an acceleration profile indicative of the corresponding foot making initial contact with the ground during the stride, determining, using the microprocessor, the corresponding shank angle at initial contact from the shank angle measurements, comparing, using the microprocessor, the shank angle at initial contact to a threshold shank angle, and identifying, using the microprocessor, an overstride of the corresponding leg if the shank angle at initial contact exceeds the threshold shank angle.

37 Claims, 18 Drawing Sheets

(51) Int. Cl.
*A61B 5/11* (2006.01)
*A61B 5/00* (2006.01)
(52) U.S. Cl.
CPC .......... *A61B 5/6828* (2013.01); *A61B 5/6832* (2013.01); *A61B 2503/10* (2013.01); *A61B 2560/0238* (2013.01); *A61B 2562/0219* (2013.01)

(56) References Cited

U.S. PATENT DOCUMENTS

| | | | |
|---|---|---|---|
| 5,955,667 | A | 9/1999 | Fyfe |
| 7,355,519 | B2 | 4/2008 | Grold et al. |
| 8,060,337 | B2 | 11/2011 | Kulach et al. |
| 8,460,001 | B1 | 6/2013 | Chuang |
| 8,573,982 | B1 | 11/2013 | Chuang |
| 8,715,208 | B2 | 5/2014 | Hodgins et al. |
| 9,227,108 | B1 | 1/2016 | Chuang |
| 2005/0107725 | A1* | 5/2005 | Wild ............ A61H 9/0071 601/152 |
| 2005/0184878 | A1 | 8/2005 | Grold et al. |
| 2007/0276270 | A1* | 11/2007 | Tran ............ A61B 5/0022 600/508 |
| 2008/0294019 | A1* | 11/2008 | Tran ............ A61B 5/0006 600/301 |
| 2011/0022349 | A1 | 1/2011 | Kulach et al. |
| 2011/0152696 | A1* | 6/2011 | Ryan ............ A61B 5/222 600/481 |
| 2013/0041617 | A1 | 2/2013 | Pease et al. |
| 2013/0131555 | A1* | 5/2013 | Hook ............ A61B 5/112 600/595 |
| 2014/0358040 | A1 | 12/2014 | Kim et al. |
| 2015/0099945 | A1 | 4/2015 | Hawkins, III et al. |

OTHER PUBLICATIONS

Lenhart, R.L. et al., "Increasing Running Step Rate Reduces Patellofemoral Joint Forces," Medicine & Science in Sports & Exercise, vol. 46, Issue 3, pp. 557-564, Mar. 2014.
Sinclair, J. et al., "Determination of Gait Events Using an Externally Mounted Shank Accelerometer," Journal of Applied Biomechanics, vol. 29, Issue 1, pp. 118-122, Feb. 2013.
Bae, J. et al, "A Soft Exosuit for Patients with Stroke: Feasibility study with a mobile off-board actuation unit," 2015 IEEE International Conference on Rehabilitation Robotics (ICORR), pp. 1-8, Aug. 11, 2015.
Lieberman, D. et al., "Effects of stride frequency and foot position in landing on braking force, hip torque, impact peak force and the metabolic cost of running in humans," Journal of Experimental Biology 218:3406-3414, Aug. 26, 2015.

* cited by examiner

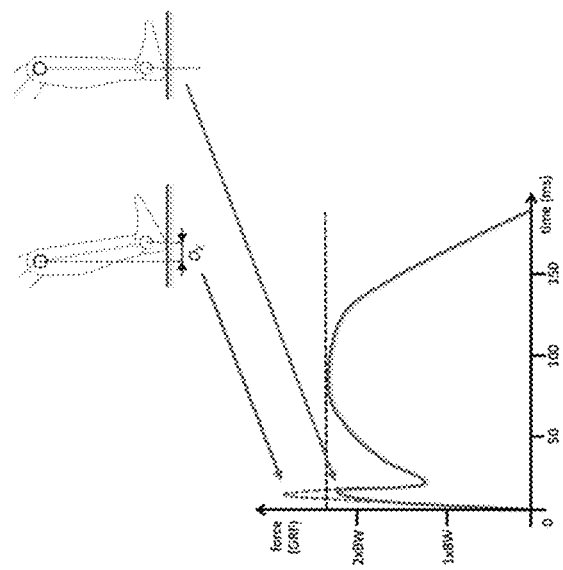
FIG. 1D
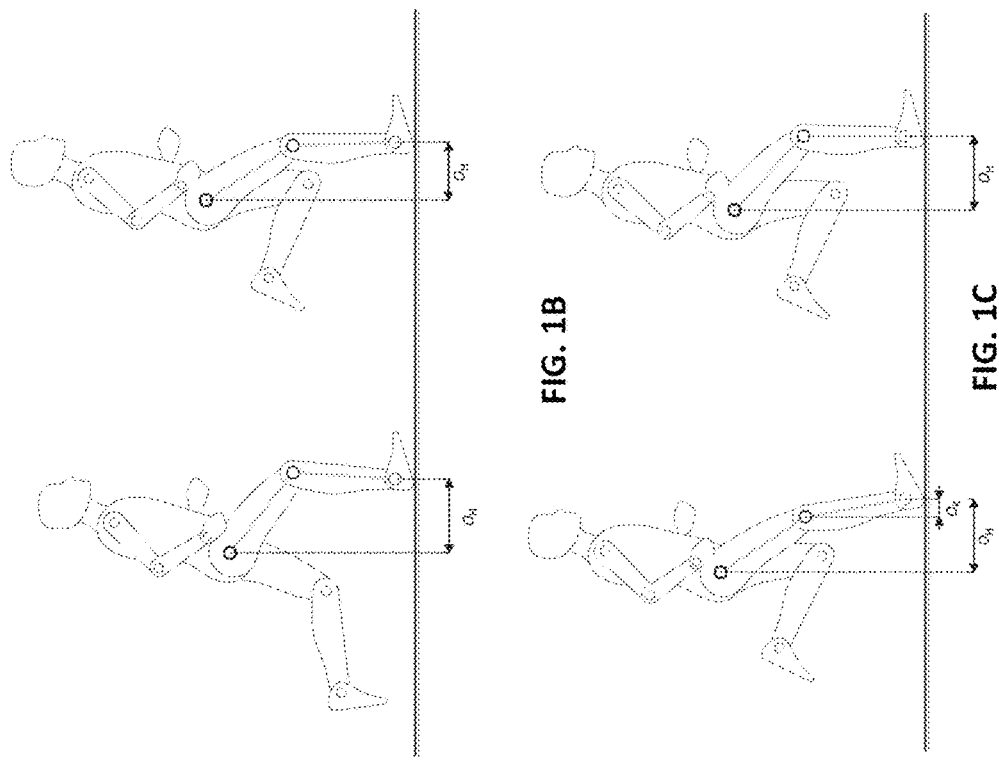
FIG. 1B
FIG. 1C

No overstride (good)

Positive overstride (bad)

Shank angle = θ

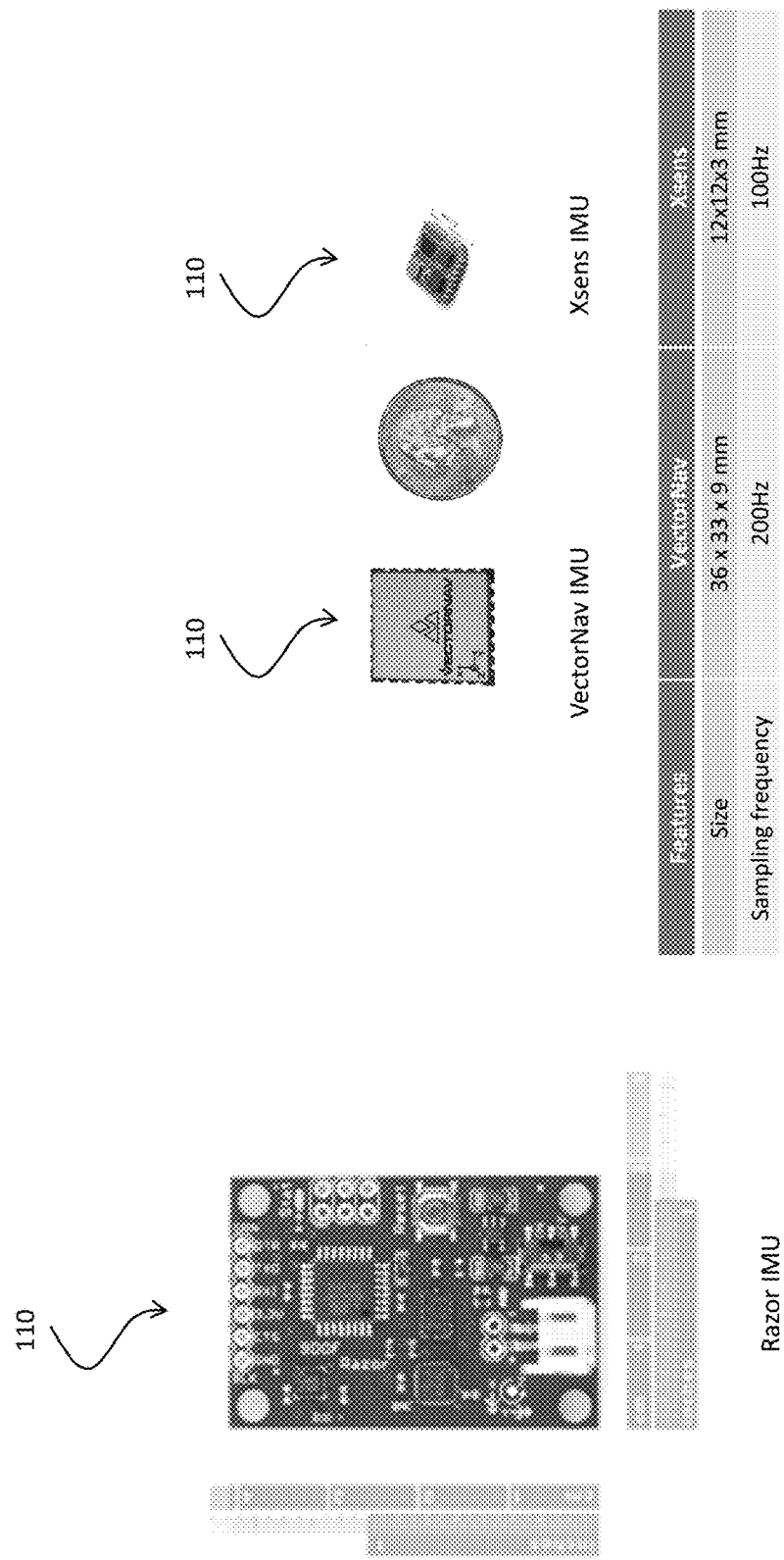

SYSTEMS AND METHODS FOR DETECTING OVERSTRIDING IN RUNNERS

RELATED APPLICATIONS

This application claims priority to and the benefit of U.S. Provisional Patent Application No. 62/138,809, filed Mar. 26, 2015, which is hereby incorporated herein by reference in its entirety for all purposes.

STATEMENT REGARDING FEDERALLY SPONSORED RESEARCH OR DEVELOPMENT

None.

FIELD

The presently disclosed embodiments relate to systems and methods for analyzing and retraining gait, and more particularly, methods and systems for identifying and correcting overstride.

BACKGROUND

As interest in running continues growing, runners are constantly seeking ways to prevent common aches and injuries. The injury rate among runners is exceptionally high compared to other popular fitness activities, with estimates reporting that around 50% of runners are injured each year. Overstriding has been shown to increase stress on the body, as overstriding leads to a straighter knee, a stiffer leg, and a more aggressive heel/foot strike, which significantly increases peak ground reaction forces and reduces the knee muscles' ability to absorb shock. The shock is then transferred to the knee menisci, knee joint and on to the hip and back joints. It also causes a greater amount of braking force that pushes the body backwards, thus causing the runner to lose speed and have to reaccelerate. Research has shown that maintaining proper running form is extremely beneficial both in reducing the chance of injury and maximizing energy efficiency.

Gait analysis has been shown to be helpful in retraining gait when overstriding is occurring. However, current technology requires training center equipment and a human analyst to perform the gait analysis within lab training centers, meaning runners are running in constructed, artificial settings. This can lead to errors in the gait analysis, since running on treadmills may differ from running in natural settings. Additionally, trainers are required to provide instruction and feedback. Because of this reliance on external equipment and human analysis, runners are not able to independently receive accurate feedback on their running form outside of the training sessions at the training centers. Examples of existing gait retraining techniques include: visual training, where a runner runs on a treadmill using mirrors or lasers for feedback; verbal feedback, where a coach or trainer monitors a runner's gait and provides instruction; and post-activity feedback, where runners capture a run with high speed cameras or motion capture systems, and analyze their form afterwards.

Other existing approaches utilize various sensor arrangements to monitor a person's gait for overstriding, without the need for visual observation by a second person or being confined to laboratory settings. However, these systems are complex, often requiring a multitude sensors on both legs in order to gather the large amounts of information necessary to detect overstriding via their respective approaches. For example, many such approaches require a full picture of how the entire leg is moving in order to determine whether the person is overstriding, and thus utilize a multitude of sensors attached to several portions of the person's leg, such as the hip, thigh, knee, shank, ankle, and/or foot. Additionally or alternatively, many such approaches require information concerning the motions of both legs of the person, and analyzing that information together, in order to determine if one or both of the person's legs are overstriding. This large amount of information must be stored and processed, and therefore require larger processors, memory capacity, and battery power. As a result, these systems tend to require complex calibration techniques to sync up the various sensors, and suffer from poor reliability when one or more of the sensors slip or drift on the person's body during locomotion. Further, these systems tend to be heavy and bulky, which can affect the person's locomotive performance and make the system more noticeable when worn or carried. Still further, the complexity of these systems can make them rather difficult and time consuming to don and take off.

Therefore, there is a need for a simple, lightweight, portable and transparent monitoring system for detecting gait overstriding.

SUMMARY

The present disclosure is directed to a method for detecting overstride in a person's gait. The method may include measuring, using an inertial measurement unit (IMU) affixed to a shank of a person, an acceleration and an angle of the shank during a stride. The acceleration measurements may be monitored using a microprocessor to detect an acceleration profile indicative of the corresponding foot making initial contact with the ground during the stride. The microprocessor may then determine, from the shank angle measurements, the corresponding shank angle at initial contact, and compare the shank angle at initial contact to a threshold shank angle. An overstride may be identified for the corresponding leg if the shank angle at initial contact exceeds the threshold shank angle.

The IMU, in various embodiments, may be positioned on a front or a side of the shank. In some embodiments, the IMU may be affixed to the shank using an anchoring member. An inner surface of the anchoring member, in some embodiments, may include an anti-slip material for frictionally engaging the shank. The anti-slip material may be patterned, in an embodiment, to provide for heat transfer and sweat wicking through corresponding portions of the anchoring member. In some embodiments, the anchoring member may include at least one of a compression sleeve and a substantially longitudinally inextensible sock.

The acceleration profile, in various embodiments, may be characterized at least in part by a rapid increase in measured acceleration. The acceleration profile, in an embodiment, may be further characterized by a relatively low acceleration magnitude leading up to the rapid increase in measured acceleration.

The shank angle, in various embodiments, may be measured in a sagittal plane. The threshold shank angle, in various embodiments, may correspond with a vertical direction of the sagittal plane. In some embodiments, the threshold shank angle may be approximately zero degrees in a coordinate system in which zero degrees corresponds with a vertical direction of the sagittal plane, positive angles correspond with a forward direction of the stride, and negative angles correspond with a rearward direction of the stride. An overstride occurs, in one such embodiment, if the shank angle at initial contact is positive. The threshold shank angle, in some embodiments, may correspond with an angle of the IMU affixed to the shank when the person is standing upright in a stationary position, and in one such embodiment, may be determined during a calibration routine prior to the stride.

The processor, in various embodiments, utilizes measurements from only the IMU affixed to the shank of a given leg in identifying an overstride of that leg.

In various embodiments, measurements are taken for a first leg and a second leg of the person, using a first IMU affixed to a first shank of the first leg, and a second IMU affixed to a second shank of the second leg of the person. In some embodiments, the method further include performing the steps of monitoring, determining, comparing, and identifying for the first leg and the second leg during the stride, utilizing shank angle and acceleration measurements from the first IMU and the second IMU. These steps, in an embodiment, may be performed for the first leg independent of the measurements from the second IMU on the second shank.

The method, in an embodiment, may further include alerting the person when an overstride is identified.

In another aspect, the present disclosure is directed to another method for detecting overstride in a person's gait. The method may include measuring, using an inertial measurement unit (IMU) affixed to a shank of a person, an angle of the shank during a stride. The shank angle measurements may be monitored using a microprocessor to identify a peak angle of the shank during the stride. The microprocessor may then compare the peak shank angle for the stride to a threshold shank angle. An overstride of the corresponding leg may be identified if the peak shank angle exceeds the threshold shank angle.

The IMU, in various embodiments, may be positioned on a front or a side of the shank. In some embodiments, the IMU may be affixed to the shank using an anchoring member. An inner surface of the anchoring member, in some embodiments, may include an anti-slip material for frictionally engaging the shank. The anti-slip material may be patterned, in an embodiment, to provide for heat transfer and sweat wicking through corresponding portions of the anchoring member. In some embodiments, the anchoring member may include at least one of a compression sleeve and a substantially longitudinally inextensible sock.

The shank angle, in various embodiments, may be measured in a sagittal plane, and in one such embodiments, may be identified as the foremost shank angle in the forward direction of the stride. The threshold shank angle, in various embodiments, may correspond with a vertical direction of the sagittal plane. In some embodiments, the threshold shank angle may be approximately zero degrees in a coordinate system in which zero degrees corresponds with a vertical direction of the sagittal plane, positive angles correspond with a forward direction of the stride, and negative angles correspond with a rearward direction of the stride. An overstride occurs, in one such embodiment, if the peak shank angle is positive. The threshold shank angle, in some embodiments, may correspond with an angle of the IMU affixed to the shank when the person is standing upright in a stationary position, and in one such embodiment, may be determined during a calibration routine prior to the stride.

The processor, in various embodiments, utilizes measurements from only the IMU affixed to the shank of a given leg in identifying an overstride of that leg.

In various embodiments, measurements are taken for a first leg and a second leg of the person, using a first IMU affixed to a first shank of the first leg, and a second IMU affixed to a second shank of the second leg of the person. In some embodiments, the method further include performing the steps of monitoring, determining, comparing, and identifying for the first leg and the second leg during the stride, utilizing shank angle measurements from the first IMU and the second IMU. These steps, in an embodiment, may be performed for the first leg independent of the measurements from the second IMU on the second shank.

The method, in an embodiment, may further include alerting the person when an overstride is identified.

BRIEF DESCRIPTION OF DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A, FIG. 1B, and FIG. 1C show various aspects of a stride;

FIG. 1D shows a graph of force versus time during a stride;

FIG. 3B and FIG. 3C depicts embodiments of an IMU in accordance with the present disclosure;

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Embodiments of the present disclosure include systems and methods for detecting overstride during various forms of locomotion, such as jogging and running. The solutions disclosed herein generally utilize a single sensor, such as an IMU, on one or both legs of a person to provide the information necessary to approximate when overstriding occurs. As a result, embodiments of the present disclosure are less complex than existing solutions, and are substantially transparent to the user due to low weight and minimal bulkiness. Further, embodiments of the present disclosure are easy and fast to don, and require simple calibration techniques compared with systems in which multiple sensors must be calibrated together to accurately read the motions of multiple joints on a single leg, and/or to account for phasing between sensors on opposing legs of the person. Further embodiments of the present disclosure may be configured to alert the person in real-time when overstriding occurs, so that the person may adjust their gait and/or cadence accordingly. Still further embodiments provide for measuring the magnitude of overstride (e.g., in degrees), so that the person may determine quantitatively how well they are improving over time. Additional advantages of the presently disclosed embodiments may be apparent to one of ordinary skill in the art in light of the teachings herein.

Figure 1A:
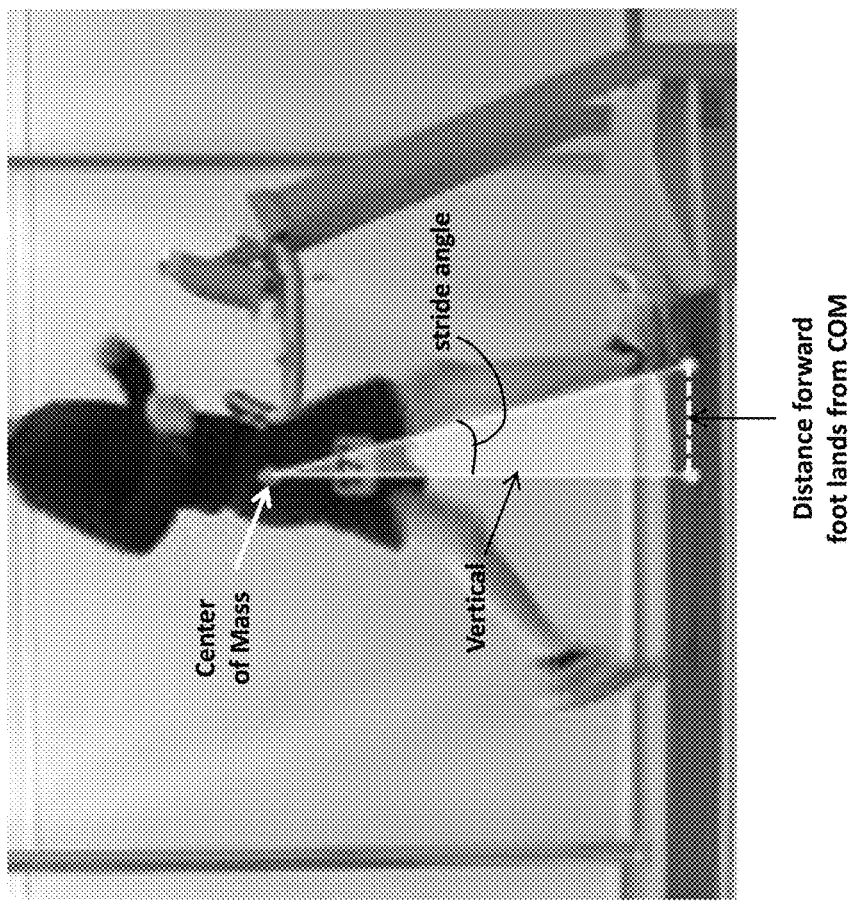

In order to better understand the biomechanics of overstriding, reference is made to FIG. 1A, FIG. 1B, and FIG. 1C, which break down various aspects of a runner's stride. Referring to FIG. 1A, overstriding is generally a function of stride angle, in that having too large of a stride angle results in the corresponding foot landing too far forward of the person's center of mass. This, in turn, often results in the person landing on their heel, rather than on their toes or mid-foot.

As shown in FIG. 1B and FIG. 1C, respectively, excessive hip flexion and excessive knee extension are contributing factors to overstriding. Referring to FIG. 1B, the effects of hip flexion angle on stride length $O_H$ are illustrated. The runner on the left strides with a larger hip flexion angle than the runner on the right, resulting in a larger stride length $O_H$, all other factors being the same. Overstriding due at least in part to excessive hip flexion can increase braking forces and increased joint torques at the ankle, knee, hip and sacroiliac joint. Referring to FIG. 1C, the effects of knee extension angle on the projected horizontal distance on the ground from the knee to the ankle (defined as $O_K$) are illustrated. The runner on the left strides with a larger knee extension angle, resulting in a larger $O_K$ and the runner landing further back on its heel, all other factors being the same. As shown in FIG. 1D, overstriding due at least in part to excessive knee extension can lead to increased peak ground reaction impact forces, which disproportionately increase the risk of knee injury. Additionally, the metabolic cost of an overstride—that is, the muscle activity required to counteract gravity and ground reaction forces—is increased with excessive hip flexion and knee extension, thereby decreasing runner performance.

Figure 2B:
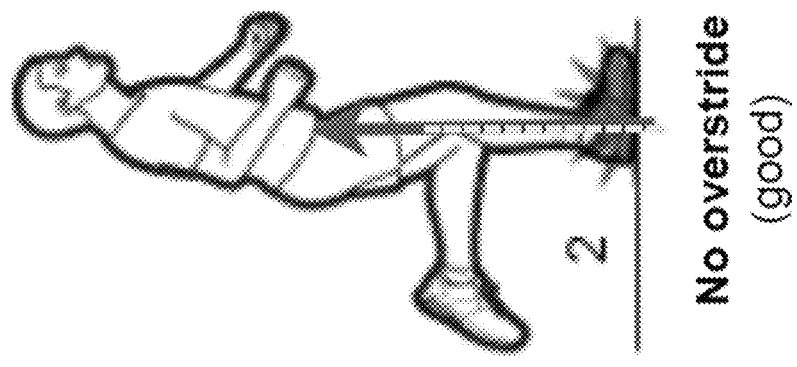
FIG. 2A and FIG. 2B demonstrate shank angles during a gait analysis.
Figure 2A:
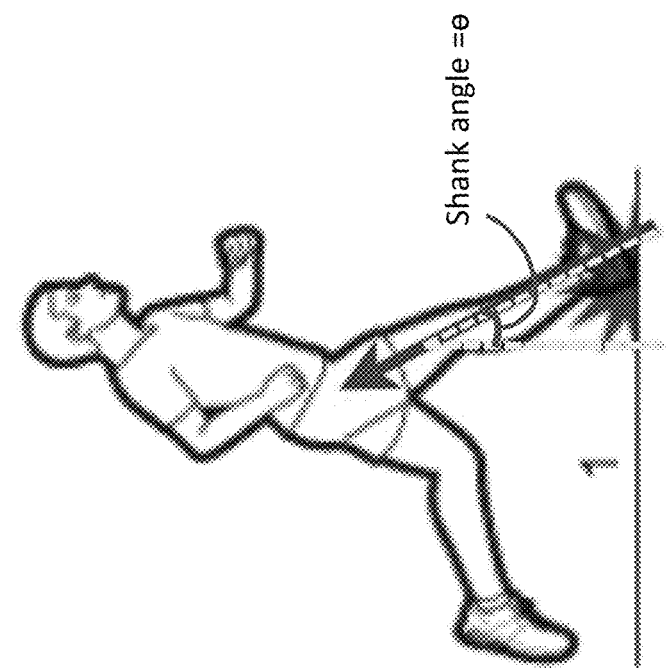

Referring to FIG. 2A and FIG. 2B, the inventors have discovered that, despite the stride length (and thus overstriding) being a function of two angles (i.e., hip flexion angle and knee extension angle), it is possible to reliably approximate overstriding by looking only at the angle of the person's shank relative to the vertical at foot touchdown. Generally speaking, if the shank is rotated forward of the vertical (i.e., rotated forward of the knee joint) in the sagittal plane when the foot strikes the ground, the person has overstrided. As shown in FIG. 2A, a positive shank angle θ (i.e., shank rotated forwards of the vertical) likely results in the person touching down on their heel, which is a key indicator of an overstriding having occurred. Conversely, as shown in FIG. 2B, a zero or negative shank angle θ (i.e., shank is vertical or rotated rearwards of the vertical) likely results in the person touching down on their mid-foot or toes in a more optimal fashion from the standpoints of at least performance and risk of injury.

The inventors have discovered that it is also possible to reliably approximate overstriding by looking only at the peak angle of the person's shank relative to the vertical during a given stride. Generally speaking, the shank swings forward to its maximum forward angle (i.e., peak shank angle) during the stride just before initial contact with the ground. As later described and shown in FIGS. 8A-8D, the strides of ten subjects were analyzed using motion capture technology, and it was discovered that peak shank angle correlated very closely with shank angle at initial contact. In particular, for peak shank angles less than 4 degrees forward from the vertical, the variation from shank angle at initial contact was less than 0.5 degrees. Even for peak shank angles exceeding 4 degrees, the variation only increased to 1.5 degrees. Accordingly, peak shank angle can be used to approximate overstriding within a tolerable margin of error. In an embodiment, any margin of error may be accounted for by adjusting the threshold shank angle (later described) for identifying overstride by a similar margin. For example, the threshold shank angle may be adjusted by 0.5 degrees when measured peak shank angle is less than 4 degrees, and adjusted by 1.5 degrees when measured shank angle is greater than 4 degrees. Of course, any suitable adjustment could be made based on any such correlation to account for any variances.

System 100

Figure 3A:
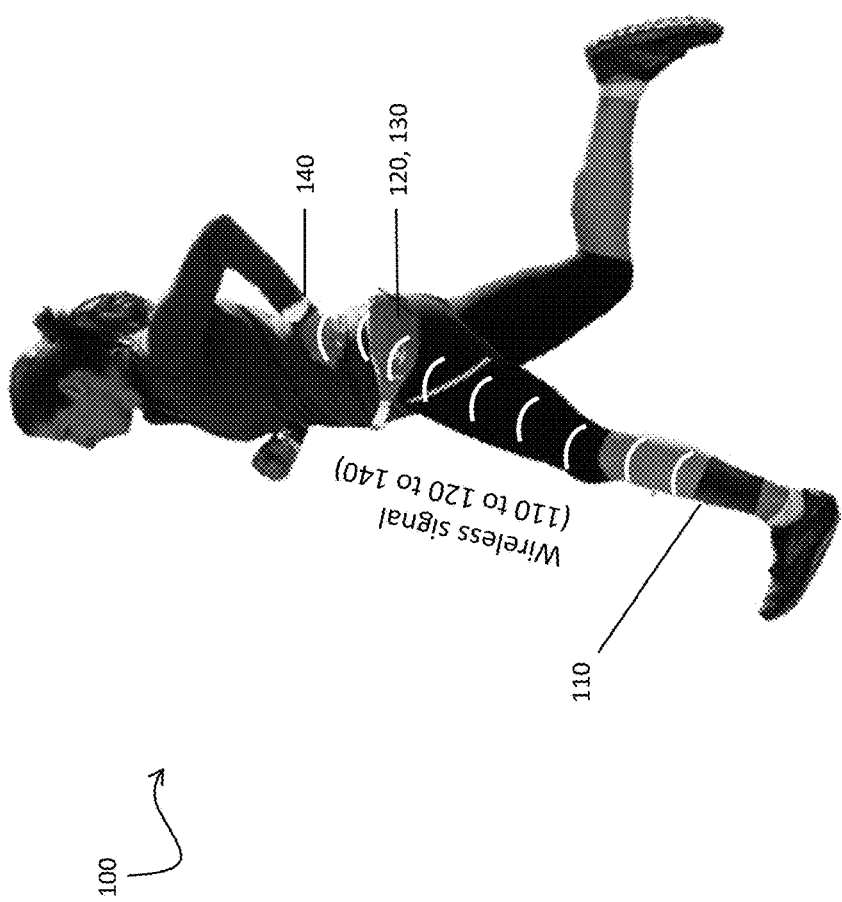
FIG. 3A depicts one embodiment of a system in accordance with the present disclosure.

Referring to FIG. 3A and FIG. 3B, system 100 of the present disclosure may comprise an inertial measurement unit (IMU) 110, a processor 120, and a memory 130. In various embodiments, system 100 may be mobile, and worn or carried by the person during a locomotion session such as a jog, run, race, or training session. In some embodiments, system 100 may further comprise a feedback device 140, as later described in more detail.

IMU 110, in various embodiments, may be affixed to one or both legs of the person. System 100, in some embodiments, may include a single IMU 110 worn on one of the person's legs, as shown in FIG. 3A. In other embodiments, system 100 may include two IMUs 110a, 110b, with the first IMU 110a being worn on one leg, and the second IMU 110b being worn on the other leg.

IMU(s) 110 may be configured for monitoring aspects of the user's gait. In particular, IMU 110 may measure inertial properties of the corresponding part of the leg, such as angle, rotational velocity, and acceleration. If not directly measured, other inertial properties may be derived from one or more of these properties, such as translation distance and translational velocity, amongst others. For ease of explanation, all such measured and derived inertial properties may collectively be referred to herein as being measured by IMU 110. One or any combination of these IMU 110 measurements, in various embodiments, may be utilized by system 100 to understand the relevant biomechanical movements of the body, and thereby detect when an overstride has occurred, as later described in more detail.

FIG. 3B depicts several representative IMUs 110 for use with system 100. Referring first to FIG. 3B, in an embodiment, IMU 110 may include a 9 degree-of-freedom Razor IMU including a MEMS triple-axis gyro, a triple-axis accelerometer, and a triple-axis magnetometer, thereby providing nine degrees of inertial measurement. In an embodiment shown in FIG. 3C, IMU 110 may include another MEMS-based IMU, such as the VN-100 IMU from VectorNav Embedded Navigation Solutions. Still referring to FIG. 3C, in yet another embodiment, IMU 110 may include a rate-integrating IMU from Xsens having triad of gyroscopes and a triad of accelerometers configured to measure linear and angular motion. While not limited as such, many of these IMUs are very small and lightweight, enabling them to be worn on the body without being noticed. For example, the VectorNav and Xsens IMUs have dimensions of 36×33×9 mm and 12×12×3 mm, respectively, making them roughly the size of a quarter, as shown. It should be recognized that the representative IMUs shown in FIG. 3B and FIG. 3C and described above are merely illustrative embodiments, and that IMU 110 may be any IMU suitable for measuring inertial properties of the body part to which they are affixed.

Microprocessor 120, in various embodiments, may be configured to monitor inertial measurements provided by IMU 110 to detect predefined criteria associated with overstriding. Upon detecting the predefined criteria, microprocessor 120 may analyze the inertial measurements to determine whether the corresponding leg has overstrided, as later described in more detail. Microprocessor 120, in some embodiments, may be further configured to process inertial measurements provided by IMU 110 for further gait analysis.

Memory 130, in various embodiments, may be configured to store executable instructions for carrying out the method 100, method 200, or any other suitable method for detecting an occurrence of overstride from IMU 110 measurements, as later described in more detail. Additionally or alternatively, memory 130, in various embodiments, may be configured to store the aforementioned predefined criteria used by microprocessor 120 to detect when overstriding occurs. Still further, in various embodiments, memory 130 may additionally or alternatively be configured to store gait information from current and/or previous locomotion sessions, as well as to store user settings such as body characteristics (e.g., person's height, weight), the type of locomotion being performed in a given locomotion session (e.g., long distance running vs. sprinting), and overstride alert preferences.

Feedback device 140, in various embodiments, may include any device configured to provide an alert to the person when he/she overstrides. In some embodiments, feedback device 140 may provide one or a combination of a visual alert (e.g., a flashing light), an audio alert (e.g., beep), and a tactile alert (e.g., vibration). Feedback device 140, in an embodiment, may further include a display for displaying the degree to which the person has overstrided, along with other relevant information such as cadence. In some embodiments, feedback device 140 may be a portable computing device, such as a smartwatch (as shown) or smartphone, or a component thereof.

The various electronic components of system 100 may be packaged in any suitable manner. For example, in an embodiment, IMU 110, microprocessor 120, and memory 130 may be packaged together into one device, configured to be positioned on the person's shank. In some embodiments, processor 120 and memory 130 may be packaged together, while IMU 110 remains separate. In this way, system 100 can be configured such that only IMU 110 (and any associated communications hardware) need be positioned on the person's shank, with the balance carried or worn elsewhere. For example, in one such embodiment, microprocessor 120 and memory 130 may be carried on the person's hips in a fanny pack, as shown in FIG. 3A. In another such embodiment, microprocessor 120 and memory 130 may be part of a smartwatch or smartphone, along with alert device 140. Of course these are merely illustrative arrangements, and the present disclosure is not intended to be limited to any particular packaging of electronic components 110, 120, 130.

Positioning of IMU 110 on the Shank

Figure 4B:
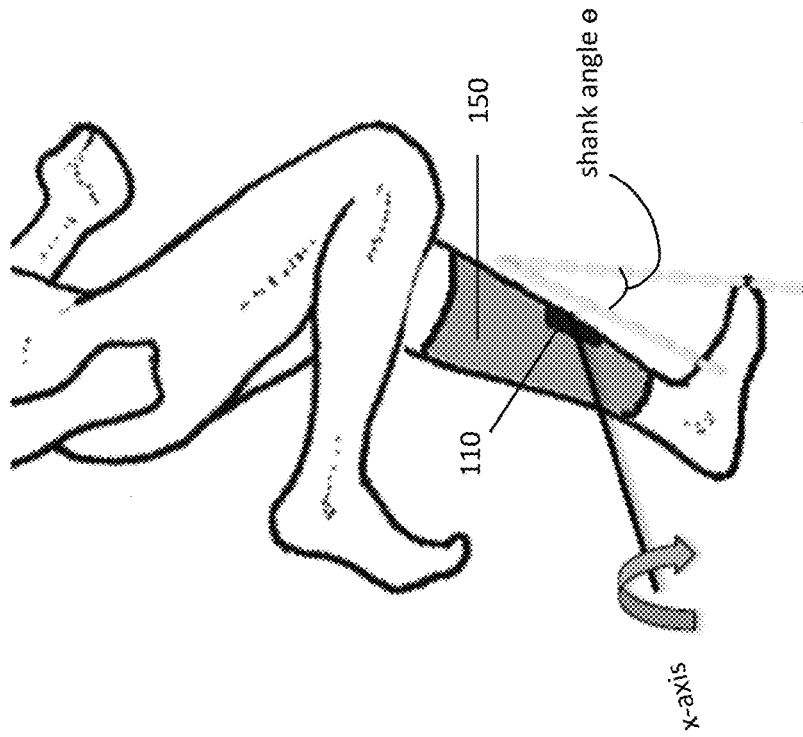
FIG. 4A and FIG. 4B illustrate positioning of an IMU on a shank of a leg in accordance with the present disclosure.
Figure 4A:
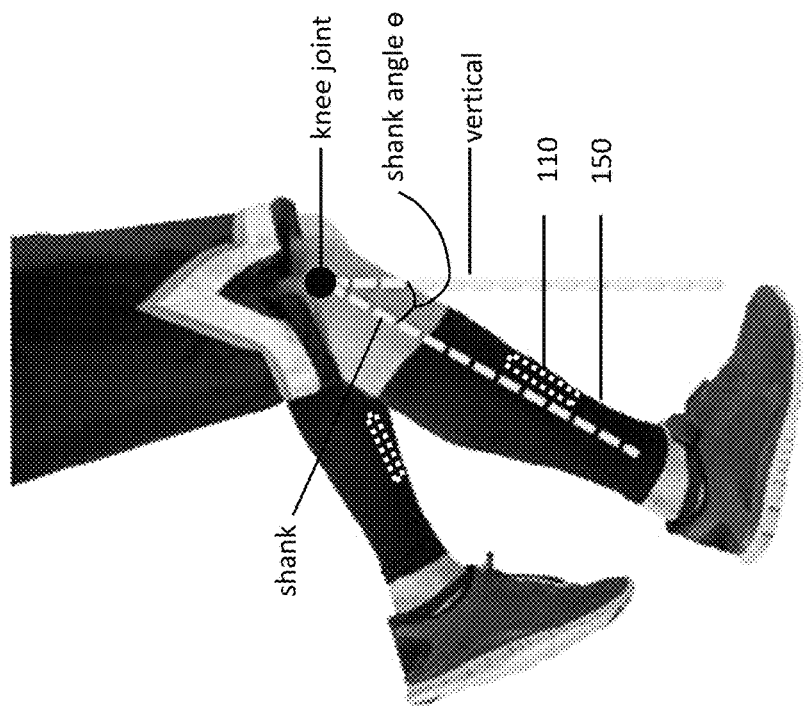

Referring to FIG. 4A and FIG. 4B, IMU 110 may be positioned on the lower portion (i.e., shank) of the person's leg or legs. As configured, IMU 110 may be used to measure an angle θ of the shank (hereinafter "shank angle θ") during locomotion.

IMU 110, in various embodiments, may be configured to measure shank angle θ in the sagittal plane of the person wearing system 100. The sagittal plane, which runs in the forwards-rearwards direction, coincides with the direction of most locomotion (e.g., jogging and running) in which overstride may be a concern. Of course, IMU 110 may additionally or alternatively be configured to measure shank angle θ in one or any combination of directions depending on the given application.

As shown in FIG. 4A and FIG. 4B, in various embodiments, IMU 110 may be configured to measure shank angle θ about the x-axis relative to the vertical. As configured, shank angle θ may be defined as the angle between the shank and the vertical direction. This provides an effective approximation of the angle of the shank relative to the person's knee joint, as shown in FIG. 4A, which as later described in more detail, may be utilized to detect when the leg overstrides during locomotion.

IMU(s) 110 of system 100, in various embodiments, may be positioned on the shank(s) of one or both legs, as shown in FIG. 4A and FIG. 4B, respectively. In particular, referring to FIG. 4A, system 100, in an embodiment, includes a first IMUs 110a positioned on the shank of the right leg, and a second IMU 110b positioned on the shank of the left leg. As configured, system 100 may be utilized to detect when an overstride occurs in either leg. This configuration may be particularly useful should asymmetries exist in the person's gait that result in one leg tending to overstride more than the other. Referring to FIG. 4B, system 100 in another embodiment, includes an IMU 110 positioned on the shank of one leg (here, the left leg). As configured, system 100 may be utilized to detect overstride in the corresponding leg only. In some embodiments, this may be sufficient as it is reasonable to assume in many cases that gait is substantially symmetrical. Stated otherwise, it can, in some applications, be assumed that if one leg overstrides, the other leg overstrides to the same or similar degree. Such a configuration may be preferred from simplicity and cost standpoints in some applications.

System 100, in various embodiments, may detect an overstride for a given leg utilizing only data provided by IMU 110 on the corresponding shank. Other measurements from other IMUs or sensors, whether on the same leg or on the other leg, need not be considered to detect overstride in the given leg in such embodiments. This, in turn, reduces the complexity of system 100, without sacrificing robust ability to detect overstride in the given leg. Such a system 100 is also fast and easy to don and calibrate, as numerous sensors need not be affixed to the person and arranged in some necessary way relative to one another. Further, by requiring only a single IMU 110 on the given leg, system 100 is very lightweight and non-bulky, thereby enhancing its transparency to the person. State otherwise, embodiments of system 100 should not noticeably affect the persons gait by its mere presence (though system 100 may be used to alert the person of overstriding and help them change their gait accordingly).

In an embodiment, IMU 110 may be positioned on the front or side of the shank (i.e., against the tibia). While shank angle is traditionally measured using the segment between the malleoli and the knee, tibia angle can be used as a suitable approximation of shank angle θ for the purposes of overstride detection in accordance with embodiments of the present disclosure. Positioning on the tibia may provide at least three advantages. First, the tibia-area of the shank lacks much soft tissue as compared to the rear of the shank (i.e., calf area). Placement in areas with minimal soft tissue can help minimize offset of IMU 110 from the tibia—i.e., the axis of the shank that runs through the knee joint and the ankle joint. As such, IMU 110 may obtain a more reliable measurement of the shank angle θ in terms of predicting whether overstriding occurs. Second, the sides and front of the shank provide a substantially non-deformable substrate against which IMU 110 may be positioned. Because of the lack of soft tissue here, IMU 110 may not tilt and/or slip as it otherwise might if placed on top of compressible tissue or contracting muscles. As such, angular readings may be more reliable. Placement in areas with minimal soft tissue can also help to minimize unwanted vibration. Third, the lack of soft tissue on the front and sides of the shank minimizes any dampening of the shock associated with foot strike. In particular, when the foot strikes the ground, the shock (which is picked up by the accelerometer in IMU 110) is transmitted up the leg. The hard, rigid, substantially non-deformable tibia provides a good transmission medium as compared to the surrounding soft tissue, which may absorb the shock and thereby diminish the ability of IMU 110 to detect the foot strike, if it were instead positioned on areas of the shank having more underlying soft tissue.

Affixing IMU 110 to the Shank

IMU 110 may be coupled with the shank of the person in any suitable manner. It should be recognized that without a secure coupling with the shank, IMU 110 may slip on the shank. Not only may this be annoying to the wearer, causing him/her to have to stop to reposition IMU 110, but slippage may also cause measurements taken by IMU 110 to drift throughout the locomotion session. This may decrease the accuracy and reliability of the measurements taken during the locomotion session, especially in cases where IMU 110 was calibrated for operation in a first position, but subsequently slips to a second different position on the shank. Accordingly, embodiments of system 100 of the present disclosure may benefit from having a secure coupling with the shank so as to keep IMU 110 from slipping.

In some embodiments (not shown), IMU 110 may simply be coupled to the shank using an adhesive. For example, the adhesive may be applied to IMU 110, and IMU 110 pressed against the skin or clothing worn by the person over the shank. It should be recognized; however, that in some such embodiments, the adhesive may cause irritate the underlying skin, leave an undesirable residue, and/or weaken in the presence of body heat and sweat.

In various other embodiments, system 100 may additionally or alternatively include an anchoring member 150 for anchoring IMU 110 to the shank. Anchoring member 150 may include any mechanism or article suitable for securely positioning IMU 110 on the shank. In some embodiments, anchoring member 150 may be configured to engage the shank through any one or combination of friction, compression, and mechanical locking with the underlying skeletal structure, musculature, and tissue.

Anchor member 150, in various embodiments, may include a textile compression sleeve, as shown in FIG. 4A and FIG. 4B. The compression sleeve may be positioned over IMU 110 (or hold IMU 110 in an integrated pocket) and, due to its elasticity, apply a normal, compressive force against the shank to hold IMU 110 in place. The compression sleeve, in an embodiment, may be made from a breathable and/or sweat wicking material to allow for body heat and sweat to escape through the fabric. In various embodiments, an inner surface of the compression sleeve may be provided or impregnated with an anti-slip material, such as silicone, to enhance the ability of the compression sleeve to frictionally engage the shank. In some such embodiments, the anti-slip material may be patterned and/or perforated to allow for heat transfer and/or sweat wicking through the anti-slip material and fabric of the compression sleeve. Additionally or alternatively, the anti-slip material may be strategically positioned on a certain portion or portions of the inner surface of the compression sleeve. For example, in an embodiment, the anti-slip material may be positioned to immediately surround IMU 110, and thereby effectively trap IMU 110 in that particular area, even if other outer portions of the compression sleeve slip on the shank. In another example, the anti-slip material may be positioned away from an upper and/or lower edge of the compression sleeve, thereby allowing for the compression sleeve to be rolled up and slid onto the shank during the donning process without the anti-slip material being exposed, and subsequently unrolled when in place such that the anti-slip material is again exposed and frictionally engages the shank. While these features are described in the context of a compression sleeve, it should be understood that any one or combination of these features may be included and leveraged in other embodiments of anchor member 150.

Anchoring member 150, in various embodiments, may be further configured to facilitate repeatably positioning the IMU 150 in the same place during consecutive locomotion sessions. By ensuring that IMU 150 is consistently positioned on substantially the same area of the shank, measurements taken by the IMU 110 may be reliably compared over time. This may allow the user to track his/her progress in retraining their stride to avoid overstriding events. Accordingly, in some embodiments, anchoring member 150 may be configured to be aligned or mechanically locked against one or more features of the shank and/or leg. These features may effectively act as reference points for repeatably positioning IMU 110 in substantially the same place over consecutive locomotion sessions. In one such embodiment, anchoring member 150 may include a sock (not shown). Lower portions of the sock, in an embodiment, may mechanically lock with body features like the toes and/or heel when pulled on, resulting in the upper portion (i.e., that portion extending up and about the shank) extending the same length up the shank every time it is worn. This may be particularly true if the sock is substantially longitudinally inextensible, such that it will not stretch significantly in a longitudinal direction. This portion of the sock may be marked to indicate where the IMU 110 should be placed, or alternatively include a pocket in which the IMU 110 may be secured. The sock, in some embodiments, may leverage feature described in the context of the compression sleeve, such as being made from a compressive material and being lined with an anti-slip material in key areas.

Measuring Shank Angle and Acceleration with IMU 110

While IMU 110 may be configured to measure a multitude of inertial properties associated with the person's leg, various embodiments of the present disclosure require only measurements of one or both of shank angle θ and acceleration for detecting overstriding, as later described in more detail. For a more complete understanding of how these properties may be measured with IMU 110, and how a foot strike may be detected therefrom, reference is made to FIG. 5A, FIG. 5B, and FIG. 5C.

Figure 5A:
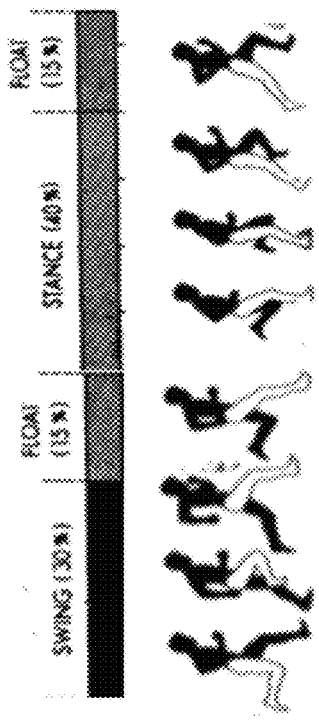
FIG. 5A illustrates a typical running cycle.

Referring to FIG. 5A for context, the various phases of a typical running cycle are illustrated and now explained. Generally speaking, a typical running cycle includes a swing phase, a first float phase, a stance phase, and a second float phase. Focusing on the right leg, the hip and knee joints flex during the swing phase, lifting the right leg off of the ground and swinging it forward from a trailing position to a leading position ahead of the left leg. For a short period of time (roughly 15% of the gait cycle), both feet are off the ground in what is called the first swing phase, just prior to the right foot making initial contact with the ground. The stance phase begins when the right foot makes initial contact, and continues as the runner's weight shifts towards the toes of the right foot prior to toe-off, and the left leg swings ahead of the right. A second float phase subsequently occurs as the right and left feet are again off the ground prior to the next running cycle.

Figure 5B:
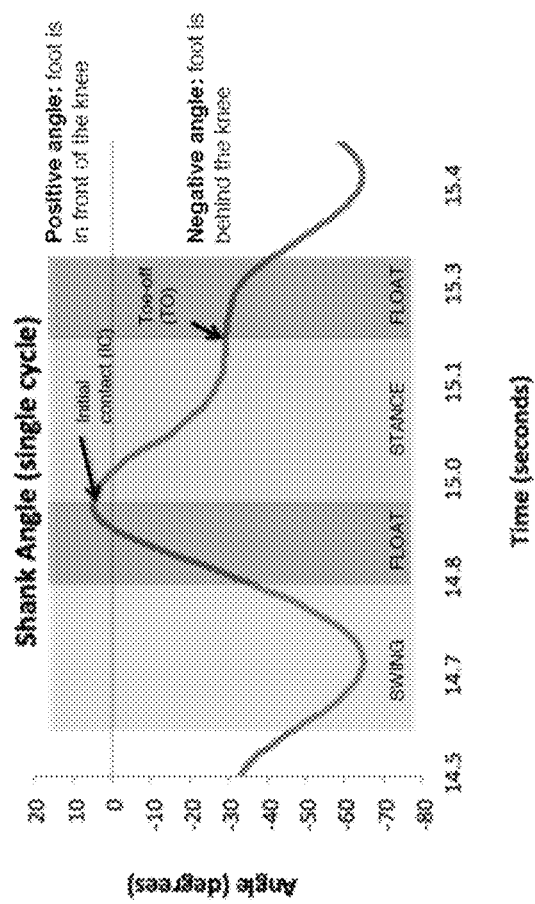
FIG. 5B graphically depicts shank angle measurements over time during a gait cycle.

FIG. 5B graphically depicts representative measurements of shank angle $\theta$ throughout a running cycle as collected by IMU 110. While only one running cycle is depicted, it should be recognized that the shank angle $\theta$ curve would follow the same general shape in subsequent running cycles. Here, the coordinate system is such that positive shank angles $\theta$ represent the time when the foot is in front of the knee, and negative shank angles $\theta$ represent the time when the foot is behind the knee.

As shown, shank angle $\theta$ is negative during the swing phase, as the knee initially flexes after toe-off and subsequently extends closer to initial contact. Knee extension continues through the float phase in anticipation of initial contact. Here, shank angle $\theta$ is shown as going positive by 5 degrees, just before initial contact, meaning that the shank is angled forward at the knee, which may cause the heel to strike the ground first at initial contact. While the foot remains on the ground throughout the stance phase, the knee and hip continue moving forward, causing shank angle $\theta$ to again become negative through toe-off and into the second float phase.

Figure 5C:
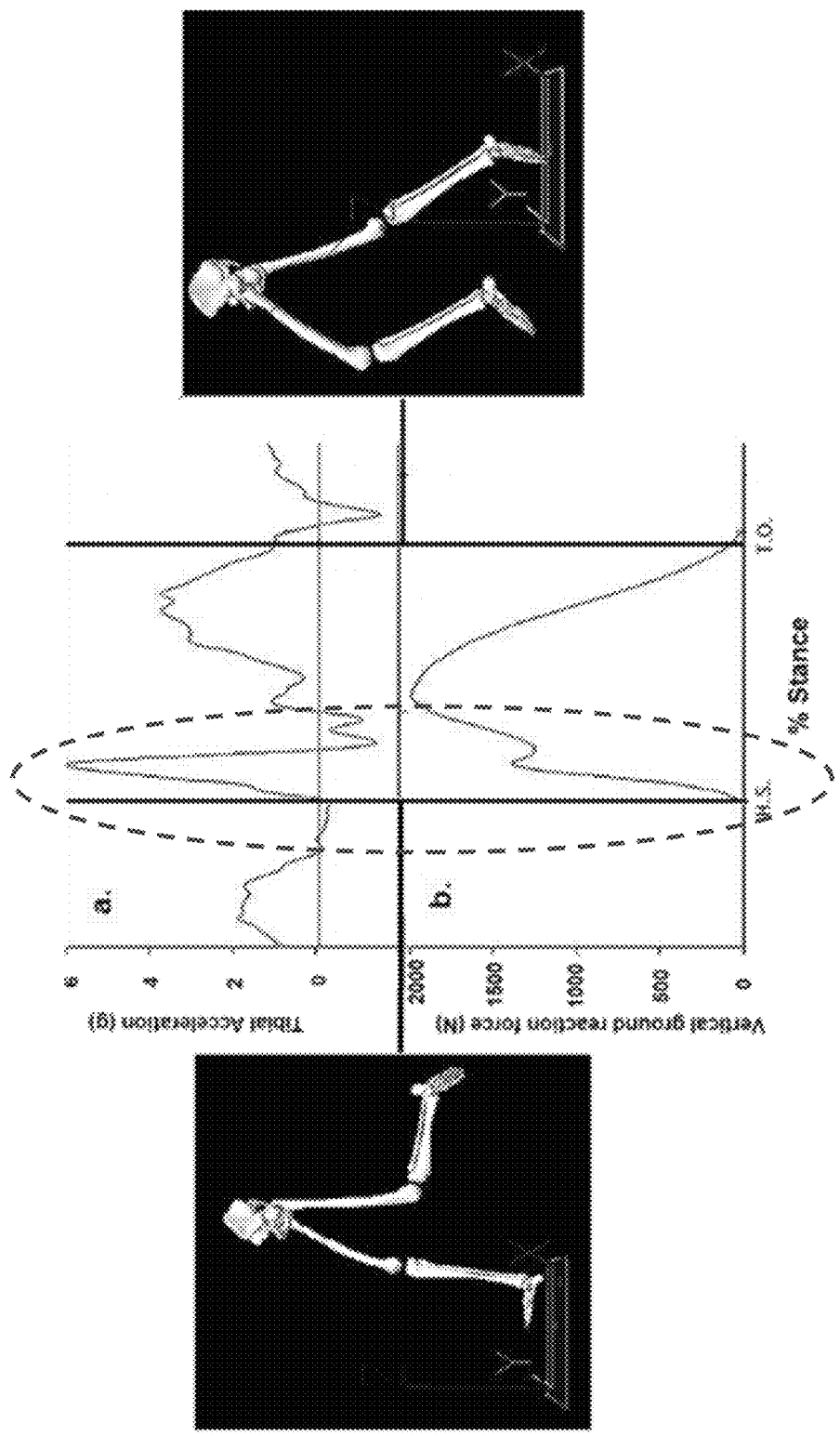
FIG. 5C graphically depicts acceleration measurements and vertical ground reaction forces experienced during a gait cycle.

FIG. 5C graphically depicts representative measurements of tibial acceleration (top) and vertical ground reaction forces (bottom) throughout the stance phase of a typical running cycle. In this particular embodiment, the tibial accelerations were collected via shank-mounted IMU 110, and the vertical ground reaction forces were measured by a force plate in a treadmill on which the test subject was running. While only one running cycle is depicted, it should be recognized that the tibial acceleration and ground reaction force curves would follow the same general shape during the stance phase of subsequent running cycles. Here, for normal running in the forward direction, the coordinate system is such that positive tibial accelerations represent knee extension, and negative tibial accelerations represent knee flexion.

As shown and indicated by the dashed oval, there is a rapid increase in tibial acceleration coinciding with the onset of ground reaction forces at initial contact. In various embodiments, processor 120 may monitor acceleration measurements from IMU 110 to detect such a spike, and thereby determine the time at which initial contact (or foot strike, as occasionally used throughout the present disclosure) occurs. In some embodiments, this may be accomplished by monitoring tibial acceleration for a spike that exceeds a threshold percentage increase relative to other accelerations typically experienced during other portions of the running cycle.

Additionally or alternatively, in some embodiments, processor 120 may monitor tibial accelerations for predetermined patterns leading up to initial contact, in order to determine that the detected spike is indeed representative of foot strike. For example, towards the end of the swing phase, acceleration is quite low, as the tibia typically slows down before initial contact. Processor 120 may be configured to confirm this pattern (i.e., low acceleration then large acceleration spike), or any other suitable pattern, as part of determining whether the large acceleration spike is associated with initial contact. In some embodiments, knowing a general profile of the acceleration values during a gait cycle could allow for using relative measurements only. In some embodiments, the acceleration profile may be along a particular single axis or could be the resultant of more than one axis.

IMU 110, in various embodiments, may require calibration to ensure accurate measurements during locomotion. In some embodiments, IMU 110 may be calibrated to determine a vertical or sagittal axis or plane while the person is at rest, allowing the IMU 110 to thereby calculate a shank angle $\theta$ within the sagittal plane. In some embodiments, calibrating 220 may further comprise determining adjustments necessary for taking measurements on uneven terrain.

Shank angle calibration, in some embodiments, may include static calibration. After putting on the IMU 110, the person may stand in a set, resting pose, and the IMU 110, using its accelerometer to know the person is at rest, may determine a vertical direction and then estimate various axes (e.g., the vertical axis). The vertical angle of the tibia/shank may be obtained when the person is standing in place, and in some embodiments, the threshold shank angle (later described) for a vertical shank may be determined during static calibration. Static calibration may be sufficient, in some embodiments, if the IMU 110 can be consistently positioned in the same place during each use.

In some embodiments, shank angle calibration may additionally or alternatively include dynamic calibration. After positioning the IMU 110, the person may stand upright, and then perform some leg movements such as raising a knee and/or moving a leg out to one side or the other. After positioning the IMU 110 and turning it on, the person may take a number of steps while data is collected from the IMU 110. Knowing that the person is walking in a straight line, the system can determine how to align the axes (e.g., the person may take 5 steps and then stop and stand for 5 seconds, or alternatively, the person could also job a little first and then stop and stand).

IMU 110 angular measurements may vary slightly across individuals (e.g., individuals may have a slight difference in leg alignment) or across different positionings of IMU 110 (e.g., the IMU 110 may be positioned in a different place, or as a result of using straps or a tightening mechanism that is adjustable the IMU 110 may be titled slightly differently in any given use). Accordingly, in various embodiments, the threshold shank angle for determining overstriding may be obtained as a part of the calibration routine each time the person dons system 100, thereby ensuring the threshold shank angle for a given session coincides with the particular positioning of IMU 110 during that session.

IMU 110 may additionally or alternatively be calibrated for acceleration measurements. When calibrating for acceleration measurements, the person may stand still for a moment and a "low" acceleration baseline is recorded with the IMU 110. Acceleration measurements at initial contact would be much higher than the acceleration baseline, as previously described. In some embodiments, acceleration calibration can be done before the IMU 110 has been positioned. Once calibration is complete, the person may begin a locomotion session, such as running, allowing the IMU 110 to start measuring acceleration and shank angles.

Methods for Detecting Overstriding Using System 100

Figure 6:
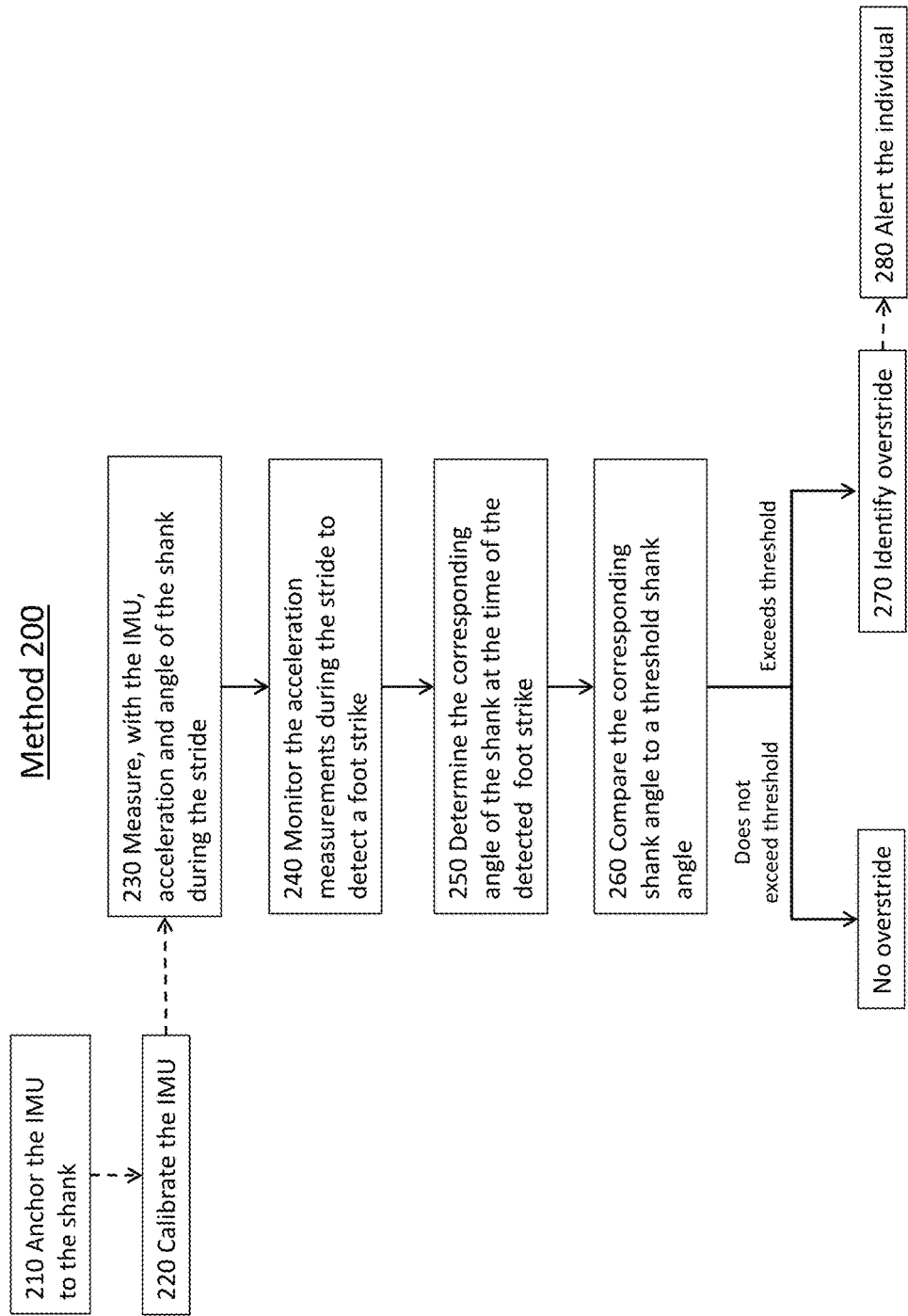
FIG. 6 is a flow chart of an embodiment of a method in accordance with the present disclosure.
Figure 7:
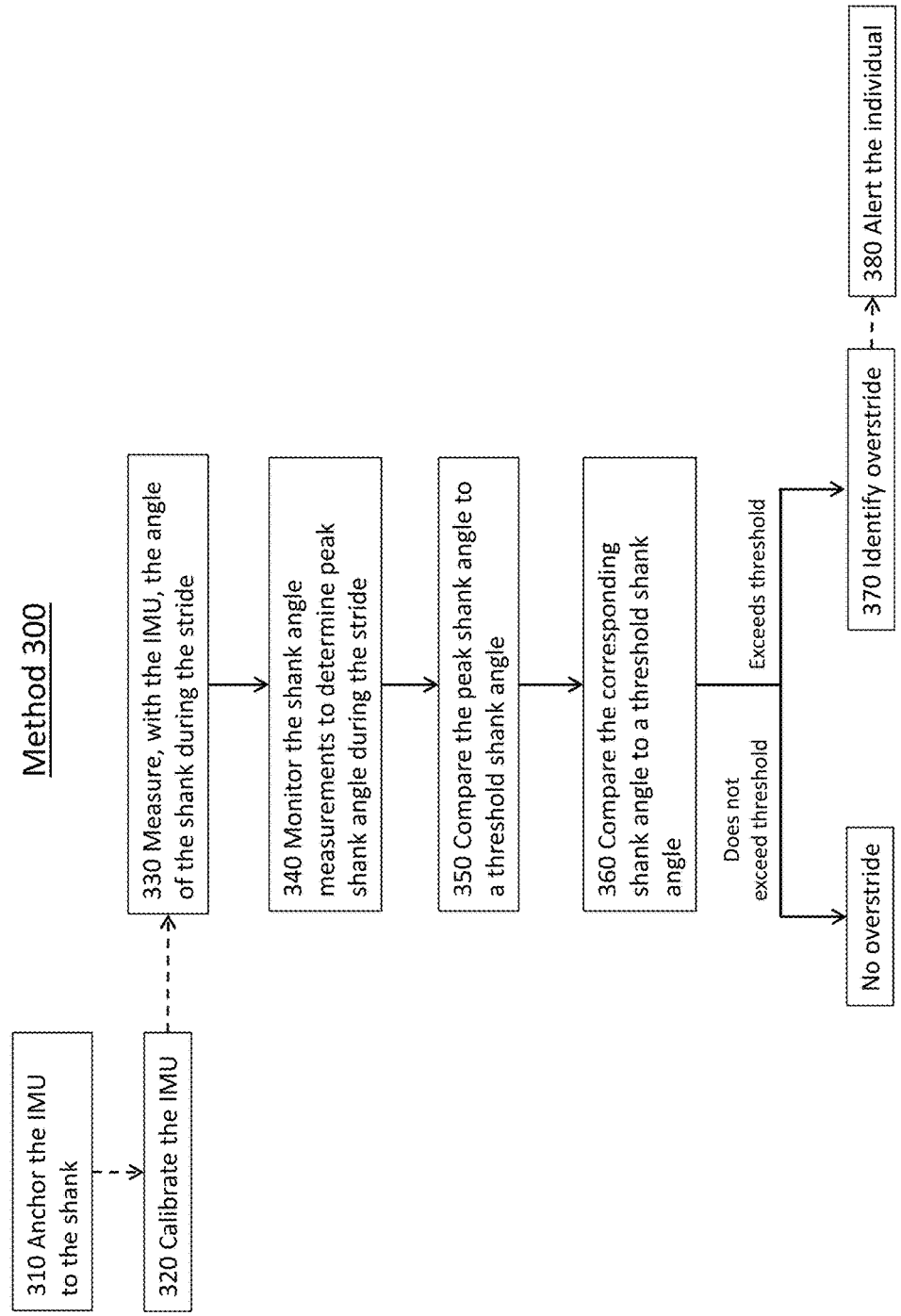
FIG. 7 is a flow chart of an alternative embodiment of a method in accordance with the present disclosure.

Referring to FIG. 6 and FIG. 7, system 100 may be utilized in various embodiments to detect overstride during locomotion. Generally speaking, IMU 110 may be utilized to measure one or both of an acceleration and an angle of the shank to which it is affixed, and processor 120 may process these measurements to detect when an overstride occurs, as described in more detail below.

FIG. 6 is a flow chart outlining steps of one exemplary method 200 of the present disclosure for detecting an overstride using measurements from IMU 110 as affixed to a shank of the person. In particular, method 200 utilizes acceleration and angle measurements from IMU 110 to detect when the corresponding leg overstrides.

Referring first to step 210, the IMU 110 may be affixed to the person's shank, as previously described. In step 220, the IMU 110 may be calibrated, as previously described, to ensure that it takes accurate inertial measurements during locomotion. Once calibrated, the person may begin the locomotion session, such as running.

Referring to step 230, throughout a given stride, the IMU 110 may take measurements of acceleration and angle of the shank. As previously described, the positioning of IMU 110 on the shank of the person allows the IMU 110 to measure the angle of the shank throughout the stride, as well as accelerations associated with the shank to which it is affixed, such as the acceleration of the shank as it moves throughout the stride, as well as accelerations associated with impacts of the corresponding foot with the ground. In various embodiments, IMU 110 may measure these inertial properties in the plane in which the person is moving, which normally would be the sagittal plane for ordinary locomotion such as jogging or running. Of course, the IMU 110 may measure these inertial properties in any suitable plane or planes, and one of ordinary skill in the art will recognize the appropriate plane(s) for a given application. The measurements may be taken at any frequency suitable for identifying, within acceptable tolerances, an acceleration profile associated with foot strike, as a well as a corresponding angle of the shank at the time foot strike occurs, as previously described. These measurements may be continuously provided to processor 120 for monitoring in step 240.

Referring to step 240, processor 120 may monitor the acceleration measurements provided by the IMU 110 for an acceleration profile indicative of the corresponding foot striking the ground. As previously described, such an acceleration profile may be characterized by one or a combination of a relatively large spike in acceleration, a spike that exceeds a threshold percentage increase, an acceleration pattern leading up to the spike (e.g., low accelerations just before initial contact and the large spike), or any other suitable identifier. In some embodiments, criteria defining the acceleration profile may be stored in memory 130, and accessed by processor 120 during the monitoring process. Processor 120 may compare the acceleration measurements against the stored parameters of the representative foot strike acceleration profile to detect when a foot strike occurs during the given stride.

Referring to step 250, upon detecting the foot strike, processor 120 may determine the corresponding angle of the shank from the shank angle measurements provided by IMU 110. In particular, in some embodiments, processor 120 may access recent shank angle measurements stored in memory 120, and identify the shank angle measurement taken at the time at which the foot strike acceleration profile occurred. In other embodiments, processor 120 may instead identify, in real-time, the corresponding shank angle immediately upon detection of the foot strike, thereby obviating the need to access stored measurements in memory 130. Regardless, in both such embodiments, the processing may be nearly instantaneous.

In some embodiments, processor 120 may temporarily store the acceleration and/or angle measurements taken during a given stride, determine the corresponding angle at the foot strike of the given stride, store the corresponding shank angle in memory 130, and clear the temporarily-stored acceleration and shank angle measurements prior to repeating the process for subsequent strides. In this way, the size of memory 130 may be minimized, thereby reducing the cost, weight, and overall size of system 100. Of course, system 100 may be configured to store any amount and combination of inertial measurements taken by IMU 110 in various embodiments. Stored data, in some embodiments, may be processed and displayed to the person on any suitable computing device (or on feedback device 140) for analysis after the person has finished the locomotion session.

Referring to step 260, processor 120 may compare the corresponding shank angle to a threshold shank angle. In some embodiments, the threshold shank angle may correspond with a vertical direction of the plane in which the person is moving (e.g., sagittal plane). For ease of understanding, in some embodiments, the vertical may be considered zero degrees, with angles forward of vertical (i.e., in the direction of motion of the person) being positive, and angles rearward of vertical (i.e., in the opposite direction) being negative. As previously described, overstride may be approximated using shank angle at the time of foot strike, with positive shank angles (e.g., about 0° to about 15°) at foot strike being indicative of overstriding, and negative shank angles (e.g., about −15° to about 0°) at foot strike being considered normal (not overstriding) in some embodiments. Accordingly, in an embodiment, the threshold shank angle may be about zero degrees. In another embodiment, the threshold shank angle may be about five degrees, for example, if it is desired to provide a small margin of error or to allow for relatively minor overstriding to go undetected.

In various embodiments, the threshold shank angle may further vary based on a variety of factors, such as the type of locomotion being performed, and the positioning of IMU 110 on the shank during the current locomotion session, amongst other factors. For example, as previously described, the threshold shank angle may be determined during the calibration routine each time the person dons system 100 to account for different positionings of IMU 110 on the body, and thus the threshold shank angle may vary accordingly. It is also conceivable that a threshold shank angle for strides associated with long-distance endurance running may be different than a threshold shank angle for strides associated with sprinting, given the different striding techniques involved. In some embodiments, the person (or a coach, athletic trainer, etc.) may adjust the threshold shank angle to suit these and other characteristics. Because the threshold shank angle is an angle, rather than a direct measure of stride length, the threshold for determining whether an overstride has occurred is independent of the height and leg length of the person. The threshold shank angle, in various embodiments, can be tuned as needed or desired to match the preferences of the user, the parameters of a given training regimen, or any other relevant factor.

Referring to step 270, if the corresponding shank angle at the time of foot strike exceeds the threshold shank angle, then processor 120 may identify that an overstriding has occurred. Processor 120, in various embodiments and as shown in step 280, may alert the person of the overstriding via feedback device 140, if equipped, as previously described. The overstriding occurrences over the course of the locomotion session may be recorded in memory 130 for processing and display to the person after the locomotion session, if desired.

FIG. 7 is a flow chart outlining steps of another exemplary method 300 of the present disclosure for detecting an overstride using measurements from IMU 110 as affixed to a shank of the person. In particular, method 300 utilizes only angle measurements from IMU 110 to detect when the corresponding leg overstrides.

Referring first to steps 310 and 320, the IMU 110 may be affixed to the person's shank and calibrated in manners similar to those described in the context of corresponding steps 210 and 220 of method 200. Once calibrated, the person may begin the locomotion session, such as running.

Referring to step 330, the IMU 110 may take measurements of the angle of the shank throughout a given stride. As previously described, the positioning of IMU 110 on the shank of the person allows the IMU 110 to measure the angle of the shank throughout the stride. In various embodiments, IMU 110 may measure shank angle in the plane in which the person is moving, which normally would be the sagittal plane for ordinary locomotion such as jogging or running. Of course, the IMU 110 may measure shank angle in any suitable plane or planes, and one of ordinary skill in the art will recognize the appropriate plane(s) for a given application. The shank angle measurements may be taken at any frequency suitable for identifying, within acceptable tolerances, the peak angle of the shank, as previously described. These measurements may be continuously provided to processor 120 for monitoring in step 340.

Referring to step 340, processor 120 may monitor the shank angle measurements provided by the IMU 110 to determine a peak angle of the shank in the direction of the person's motion during the stride. In particular, in various embodiments, processor may monitor the magnitude and sign of the shank angle measurements for when the magnitude peaks in the proper sign direction. For example, assuming the coordinate system used for shank angle measurements calls the vertical zero degrees, and angles forward of vertical as positive angles, processor 120 may monitor determine peak shank angle as the highest magnitude shank angle of positive sign during the given stride.

Processor 120 may periodically access recent shank angle measurements stored in memory 120, and identify the peak shank angle measurement for the given stride. In other embodiments, processor 120 may instead identify, in real-time, the peak shank angle, thereby obviating the need to access stored measurements in memory 130. Regardless, in both such embodiments, the processing may be nearly instantaneous.

In some embodiments, processor 120 may temporarily store the shank angle measurements taken during a given stride, determine the peak shank angle of the given stride, store the peak shank angle in memory 130, and clear the temporarily-stored shank angle measurements prior to repeating the process for subsequent strides. In this way, the size of memory 130 may be minimized, thereby reducing the cost, weight, and overall size of system 100. Of course, system 100 may be configured to store any amount and combination of inertial measurements taken by IMU 110 in various embodiments. Stored data, in some embodiments, may be processed and displayed to the person on any suitable computing device (or on feedback device 140) for analysis after the person has finished the locomotion session.

Referring to step 360, processor 120 may compare the peak shank angle to a threshold shank angle. In some embodiments, the threshold shank angle may correspond with the maximum shank angle typically reached in non-overstriding situations. For ease of understanding, in some embodiments, the vertical may be considered zero degrees, with angles forward of vertical (i.e., in the direction of motion of the person) being positive, and angles rearward of vertical (i.e., in the opposite direction) being negative. As previously described, overstride may be approximated using peak shank angle, with peak shank angles greater than about 0° being indicative of overstriding in some embodiments, and peak shank angles less than about 0° being considered normal (not overstriding). Accordingly, in an embodiment, the threshold shank angle may be about zero degrees. In another embodiment, the threshold shank angle may be about five degrees, for example, if it is desired to provide a small margin of error or to allow for relatively minor overstriding to go undetected.

In various embodiments, the threshold shank angle may further vary based on a variety of factors, such as the type of locomotion being performed, and the positioning of IMU 110 on the shank during the current locomotion session, amongst other factors. For example, as previously described, the threshold shank angle may be determined during the calibration routine each time the person dons system 100 to account for different positionings of IMU 110 on the body, and thus the threshold shank angle may vary accordingly. It is also conceivable that a threshold shank angle for strides associated with long-distance endurance running may be different than a threshold shank angle for strides associated with sprinting, given the different striding techniques involved. In some embodiments, the person (or a coach, athletic trainer, etc.) may adjust the threshold shank angle to suit these and other characteristics. Because the threshold shank angle is an angle, rather than a direct measure of stride length, the threshold for determining whether an overstride has occurred is independent of the height and leg length of the person. The threshold shank angle, in various embodiments, can be tuned as needed or desired to match the preferences of the user, the parameters of a given training regimen, or any other relevant factor.

Referring to step 370, in some embodiments, if the peak shank angle exceeds the threshold shank angle, then processor 120 may identify that an overstriding has occurred. In other embodiments, peak shank angle could be determined during several strides, and compared on a stride-by-stride basis. In still further embodiments, peak shank angle measurements could be averaged over a number of strides, and then compared against the threshold shank angle or with averages from other strides. Such an approach may be similarly used in method 200, and may serve to reduce the effect of measurement errors, as well as take into account small variations in terrain. Processor 120, in various embodiments and as shown in step 380, may alert the person of the overstriding via feedback device 140, if equipped, as previously described. The overstriding occurrences over the course of the locomotion session may be recorded in memory 130 for processing and display to the person after the locomotion session, if desired.

Methods 200 and 300, in various embodiments, may be performed for one or both legs of the person throughout the locomotion session. In particular, in embodiments including just one IMU 110, being affixed to one of the legs of the person, method 300 may be configured to monitor IMU 110 to detect overstride in the corresponding leg. Methods 200 and 300 may be configured such that the user is alerted to overstriding of that leg, and possibly alerted again at the estimated time the other leg would assuming overstride on its next step. This timing may be estimated based on the average cadence of the person leading up to the event. This cadence may be determined as the time between detected foot strikes for the leg on which the IMU 110 is affixed. In embodiments including two IMUs 110 (i.e., a first IMU 110 on the shank of the right leg, and a second IMU 110 on the shank of the left leg), methods 200 and 300 may be configured such that processor 120 (or two processors 120) monitor IMUs 110 independent of one another to independently detect overstride in the corresponding legs.

In various embodiments, processor(s) 120 in methods 200 and 300 may consider measurements from both first and second IMUs 110 in determining whether one of those legs has overstrided. One of ordinary skill in the art will recognize suitable applications in light of the present disclosure.

Test Validation

Testing was performed to validate embodiments of the systems and methods described herein. Measurements were performed in a motion capture lab equipped with eight (8) infrared cameras (by OQUS™) and a treadmill equipped with two forceplates (Bertec, OH). Thirteen markers were placed in biomechanically relevant places of an individual: the right and left posterior superior iliac spine, the right and left anterior superior iliac spine, the right greater trochanter, the right medial and lateral knee, the anterior tibia, the lateral and medial malleoli, the calcaneus, and the first and fifth metatarsal phalanges. This allows for the results from the IMU system to be compared to a reconstructed profile of the individual's motion, allowing a comparison between the overstride angles calculated by the motion capture software (QUALISYS® and Visual 3D™) and the angles reported by the IMU device. The force plate data is also helpful in determining when initial contact occurred, and for further developing the algorithm.

Figure 8A:
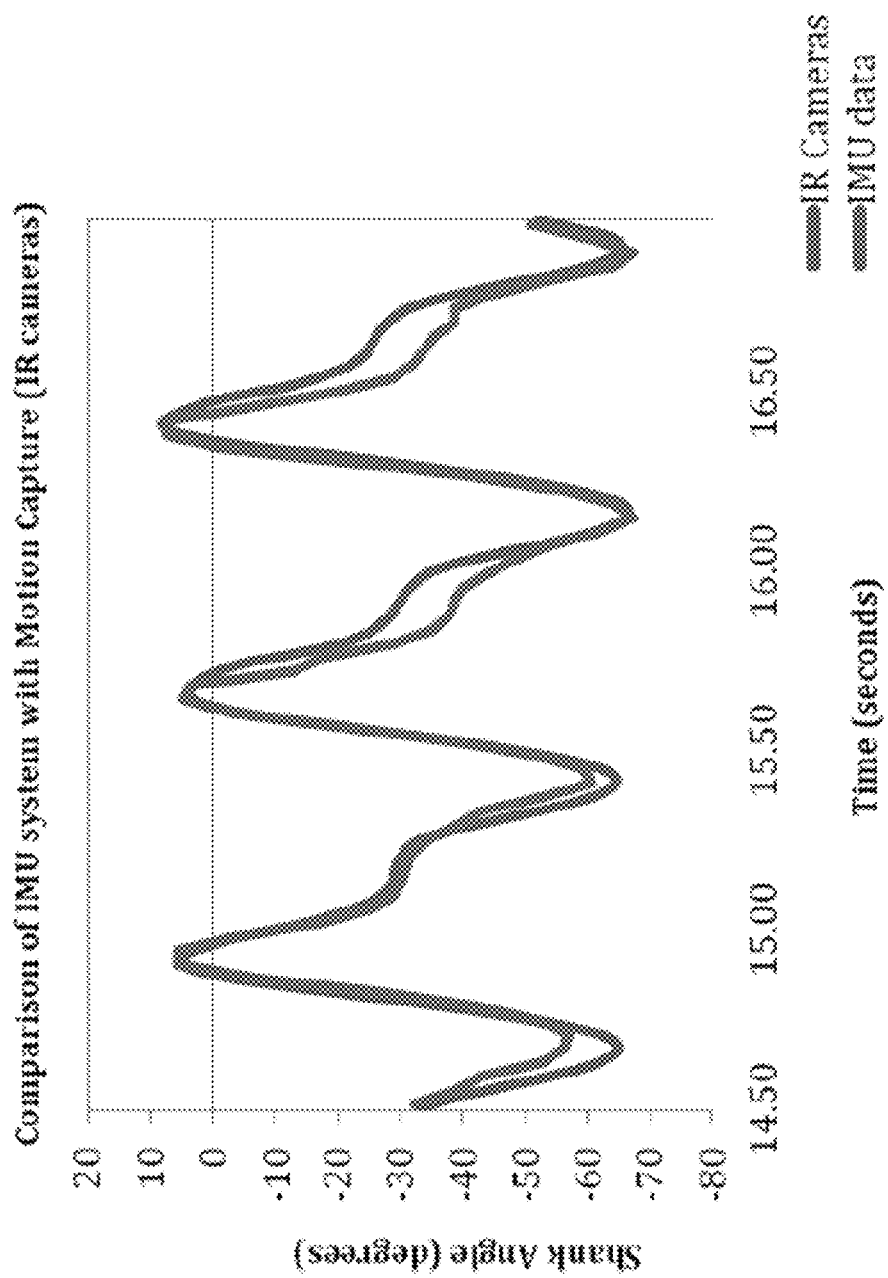
FIG. 8A graphically compares shank angle measurements taken with an IMU and an IR camera, in accordance with the present disclosure.

Comparisons of the angle reported by the IMU system and QUALISYS® motion capture for three strides are shown in FIG. 8A. FIG. 8A shows a comparison of the shank angle calculated based on analysis of data measured by the IMU system with the shank angles calculated by the IR camera motion capture system (using OQUS™ cameras and QUALISYS® system). The readings from the IMU system are shifted to account for the proper coordinate system. For the analysis and classification of degree of overstride, the peak of these shank angle curves provide valuable insight, since that is closer to where initial contact occurs (as described in greater detail herein below). As can be observed from the plot of FIG. 8A, the readings from the IMU system correlate very well (and fairly matches) the motion capture system around this peak. This indicates that the method of using a single angle around the x-axis of the IMU is valid in estimating and quantifying the degree of overstride.

Figure 8B:
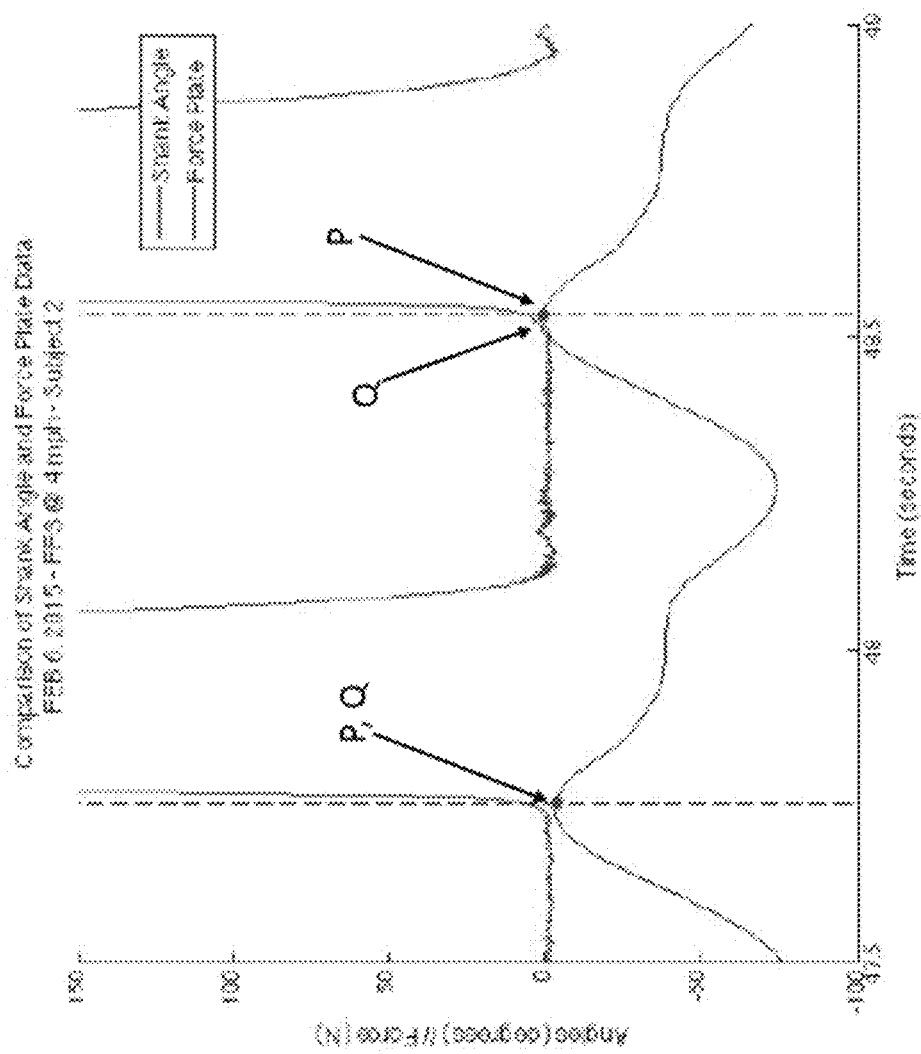
FIG. 8B, FIG. 8C, and FIG. 8D graphically compare IMU shank angle measurements with force plate data in accordance with the methods of the present disclosure.
Figure 8C:
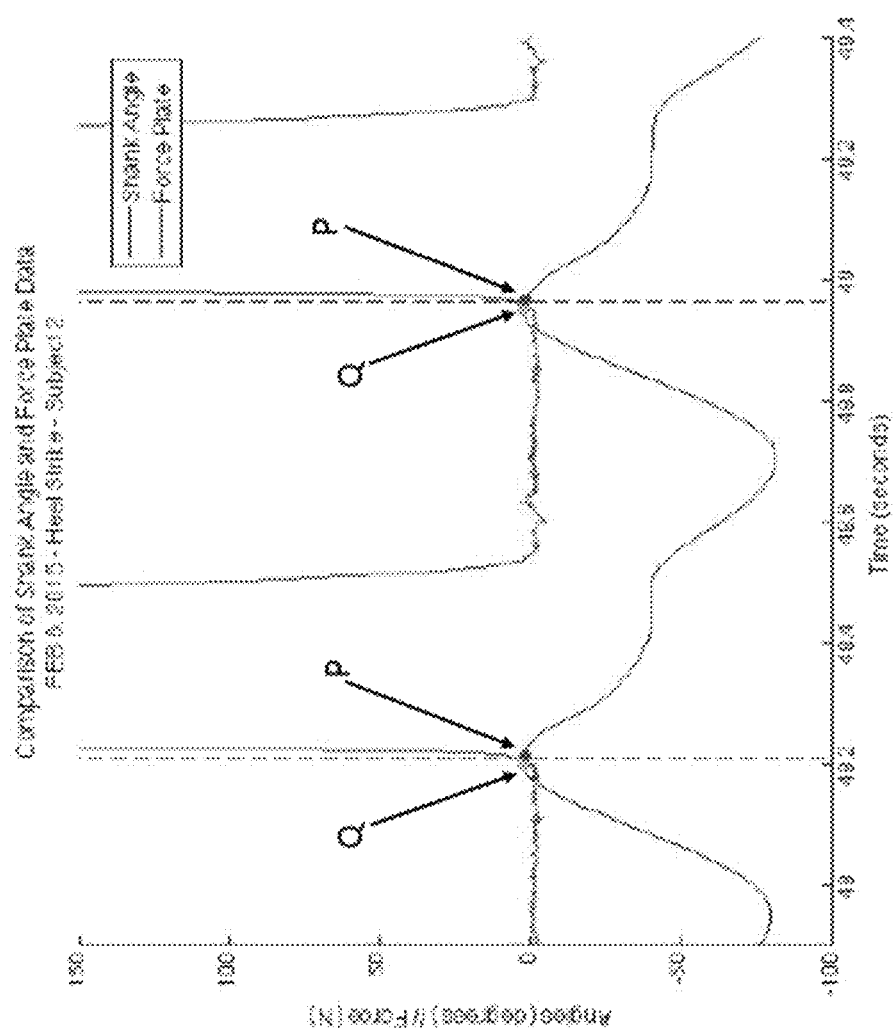
Figure 8D:
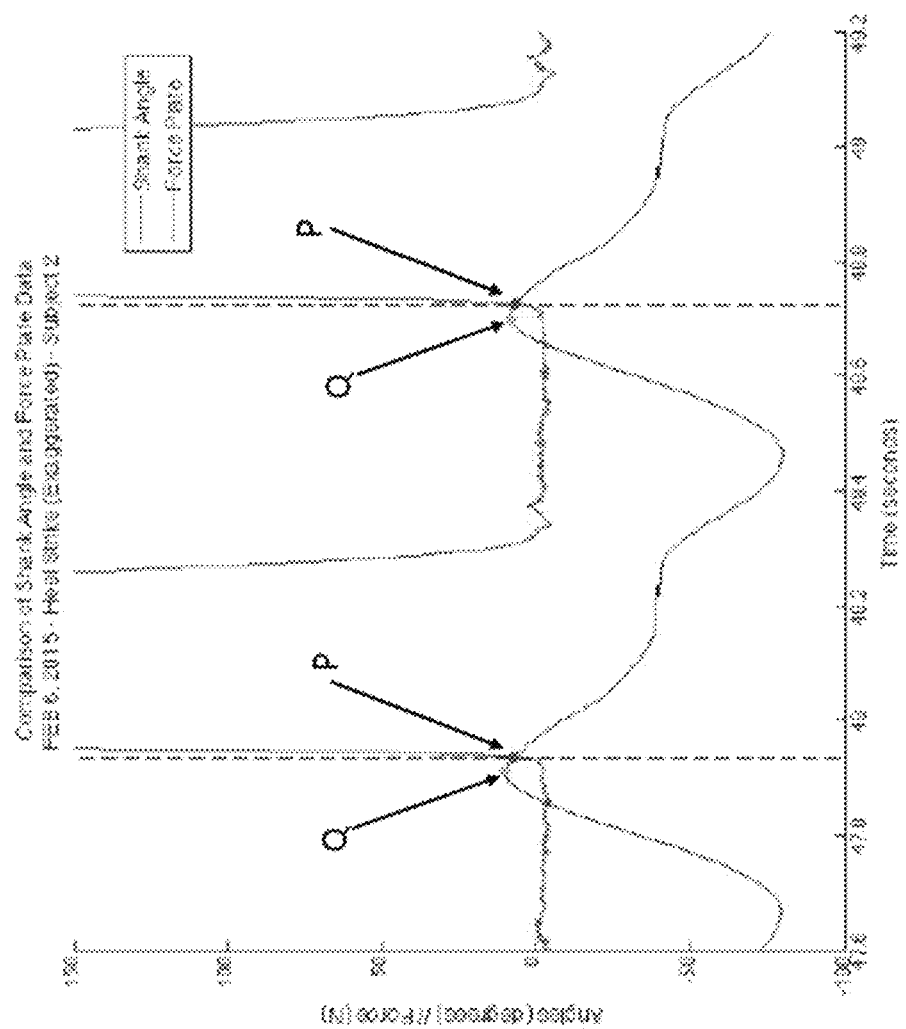

It is also determine when initial contact occurs. For this, the shank angles are compared to force plate data. The point the force plate first reads 10 N defines initial contact, and shank angle is calculated at this point. This angle represents the overstride angle at impact. The angle is indicated at the arrows labeled "P" in FIG. 8B and FIG. 8C. FIG. 8B shows data from an individual running with a forefoot strike (very little overstride). FIG. 8C shows data from an individual running with a slight heel strike (more overstride). FIG. 8D shows data from an individual running with an exaggerated heel strike (even more overstride). The data shows that the overstride angle appears very closely to the peak of the shank angle cycle, indicated at the arrows labeled "Q" in FIG. 8A, FIG. 8B and FIG. 8C show that the relevant overstride angle and the peak angle differs based on the magnitude of overstride.

FIG. 8A overlays the shank angle data with the force plate data from the treadmills for a forefoot strike. The black dotted line represents initial contact (IC), and the dot on the curve indicated by the arrows labeled "P" represents the shank angle at IC. The peak of the shank angle curve is indicated by the dot on the curve indicated by the arrows labeled "Q".

FIG. 8B overlays the shank angle data with the force plate data from the treadmills for a slight heel strike. The black dotted line represents initial contact (IC), and the dot on the curve indicated by the arrows labeled "P" represents the shank angle at IC. The peak of the shank angle curve is indicated by the dot on the curve indicated by the arrows labeled "Q". Compared to the forefoot strike in FIG. 8A, the difference between the dot indicated by the arrows labeled "P" and the dot indicated by the arrows labeled "Q" has grown.

FIG. 8C overlays the shank angle data with the force plate data from the treadmills for an exaggerated heel strike. The black dotted line represents initial contact (IC), and the dot on the curve indicated by the arrows labeled "P" represents the shank angle at IC. The peak of the shank angle curve is indicated by the dot on the curve indicated by the arrows labeled "Q". Compared to the strikes in FIG. 8A and FIG. 8B, the difference between the dot indicated by the arrows labeled "P" and the dot indicated by the arrows labeled "Q" has grown. It can also be observed that the peak angle is of a higher value as well.

This data demonstrates that as the peak angle increases, the difference between the relevant overstride angle and peak angle increases as well. This is consistent from a biomechanical perspective, because an increased peak shank angle means the individual is reaching further forward with their foot, likely over-reaching and preparing for a heel-strike, and needs to pull their foot back slightly before landing in order to maintain balance. This pullback is also recorded with high-speed video capture. The developed algorithm takes this phenomenon into account by detecting the peak angle, processing its magnitude, and then making the appropriate corrections to evaluate overstride.

Figure 9A:
FIG. 9A is an embodiment of an IMU contained in a compression sleeve in accordance with the present disclosure.
Figure 9B:
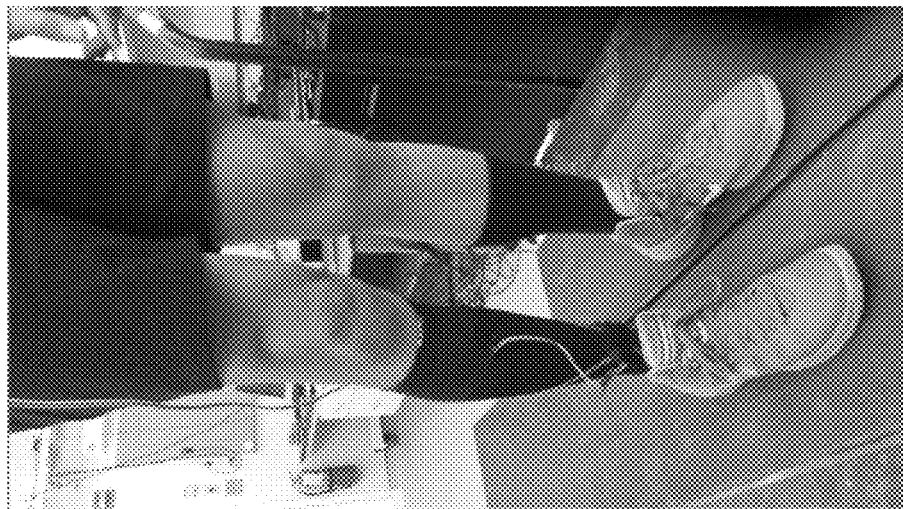
FIG. 9B and FIG. 9C show positioning of the compression sleeve containing the IMU.
Figure 9C:
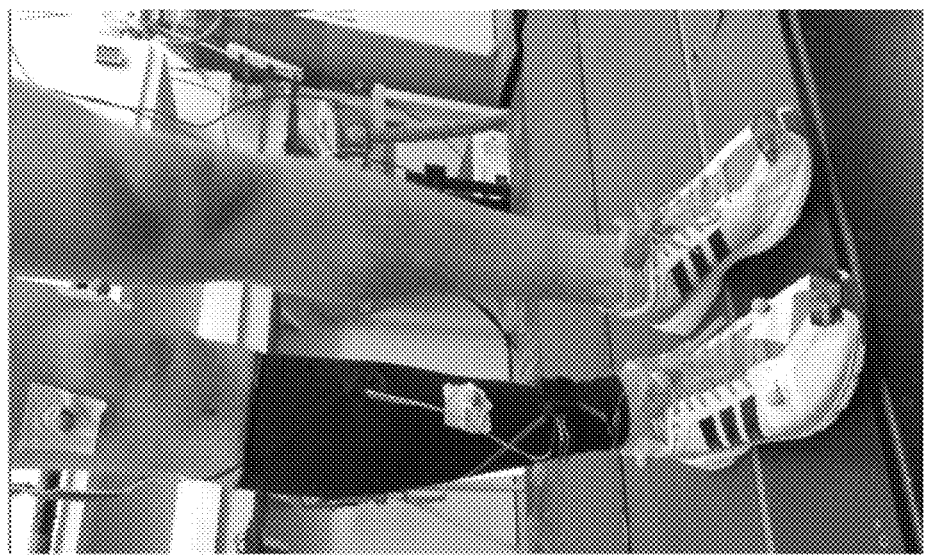
Figure 9D:
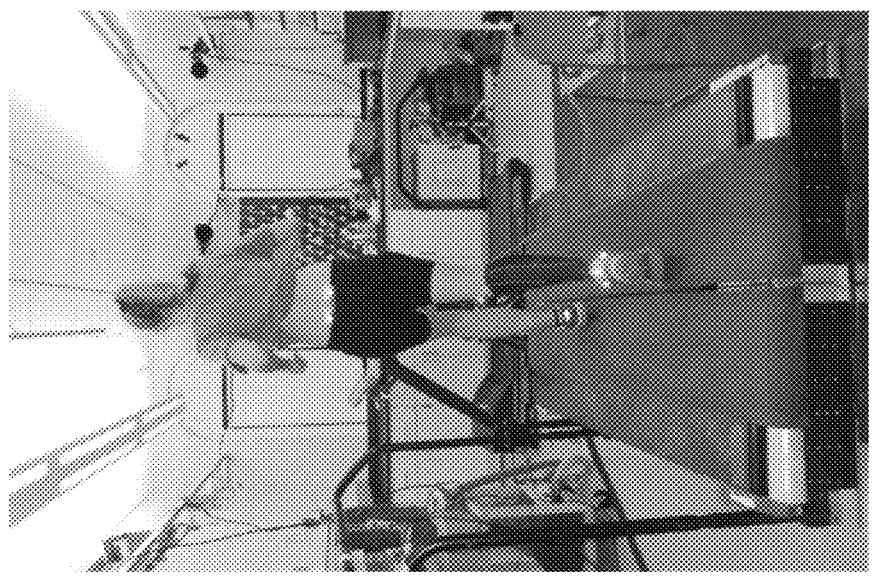
FIG. 9D show an embodiment of a gait analysis using an embodiment of the system in accordance with the present disclosure.

An embodiment of a system for monitoring overstride is demonstrated in FIG. 9A, FIG. 9B, FIG. 9C and FIG. 9D. An IMU, for example be a razor IMU, is attached to body with a compression sock (FIG. 9A) having a pocket for holding the IMU goes. The IMU is therefore easily removable for washing. The compression sock can be pulled on over the foot and this can help make sure the IMU is roughly in the right location and may be repeatedly positioned at the same spot on the shank. As shown in FIG. 9B and FIG. 9C, the IMU is positioned in the sock such that the IMU is located on a front lower part of the shank. The system is therefore a low profile system, and as seen in FIGS. 9B and 9C and demonstrated in FIG. 9D, the IMU is wired to allow for testing in a lab.

In an embodiment (not pictured), the IMU is positioned on the lower part of shank, placed less on front and more to the outside of the leg. The microprocessor, the IMU, a battery and any wireless communication are miniaturized so as to be all in a contained package that fits within a sleeve or other container that may be part of a compression sock or other article of clothing. The IMU may also be attached to the shank with a custom brace/wrap/strap that can be put on after a shoe is worn, which may further include (1) a mechanism that allows the IMU to conform to the leg, and (2) some form of compression to secure it in place. Alternatively, or additionally, a frictional material may be used to mitigate sliding, allowing for the IMU and any accompanying electronics to be securely attached to the person via the material. The material may be neoprene foam or any similar material that helps provide a solid mechanical contact to the shank. The IMU may, in some embodiments, have a calibration routine such that precise placement of the IMU is not required. The IMU may further have markings on it so a wearer will know how to roughly align a marker on the brace with a body part or forward direction.

In some embodiments, the IMU is mounted higher up the shank on the front of the tibia on a part of shank without too much soft tissue. The IMU is mounted with a calf wrap type anchor that is just around the top of the shank and mechanically locks to the shape of the calf. In some embodiments, the IMU could be put on as a wrap or else pulled on over foot.

While the presently disclosed embodiments have been described with reference to certain embodiments thereof, it should be understood by those skilled in the art that various changes may be made and equivalents may be substituted without departing from the true spirit and scope of the presently disclosed embodiments. In addition, many modifications may be made to adapt to a particular situation, indication, material and composition of matter, process step or steps, without departing from the spirit and scope of the present presently disclosed embodiments. All such modifications are intended to be within the scope of the claims appended hereto.

What is claimed is:

1. A method for detecting overstride, the method comprising:
    measuring, using an inertial measurement unit (IMU) affixed to a shank of a person, an acceleration and an angle of the shank during a stride;
    monitoring, using a microprocessor, the shank acceleration measurements to detect an acceleration profile indicative of the corresponding foot making initial contact with the ground during the stride;
    determining, using the microprocessor, the corresponding shank angle at initial contact from the shank angle measurements;
    comparing, using the microprocessor, the shank angle at initial contact to a threshold shank angle;
    identifying, using the microprocessor, an overstride of the corresponding leg if the shank angle at initial contact exceeds the threshold shank angle.

2. The method of claim 1, wherein the IMU is positioned on a front or a side of the shank.

3. The method of claim 1, wherein the IMU is affixed to the shank using an anchoring member.

4. The method of claim 3, wherein an inner surface of the anchoring member includes an anti-slip material for frictionally engaging the shank.

5. The method of claim 4, wherein the anti-slip material is patterned to allow for heat transfer and sweat wicking through corresponding portions of the anchoring member.

6. The method of claim 3, wherein the anchoring member includes at least one of a compression sleeve and a substantially longitudinally inextensible sock.

7. The method of claim 1, wherein in the step of measuring, the shank angle is measured in a sagittal plane.

8. The method of claim 1, wherein in the step of monitoring, the acceleration profile is characterized at least in part by a rapid increase in measured acceleration.

9. The method of claim 8, wherein the acceleration profile is further characterized by a relatively low acceleration magnitude leading up to the rapid increase in measured acceleration.

10. The method of claim 1, wherein in the step of comparing, the threshold shank angle corresponds with a vertical direction of the sagittal plane.

11. The method of claim 1, wherein the threshold shank angle is approximately zero degrees in a coordinate system in which zero degrees corresponds with a vertical direction of the sagittal plane, positive angles correspond with a forward direction of the stride, and negative angles correspond with a rearward direction of the stride.

12. The method of claim 11, wherein in the step of identifying, an overstride occurs if the shank angle at initial contact is positive.

13. The method of claim 1, wherein in the step of comparing, the threshold shank angle corresponds with an angle of the IMU affixed to the shank when the person is standing upright in a stationary position.

14. The method of claim 13, further including the step of determining the threshold shank angle during a calibration routine prior to the stride.

15. The method of claim 1, wherein in the step of identifying, the processor identifies an overstride of the corresponding leg utilizing measurements from only the IMU affixed to the shank of the corresponding leg.

16. The method of claim 1, wherein the step of measuring is performed for a first leg and a second leg of the person, using a first IMU affixed to a first shank of the first leg of a person, and a second IMU affixed to a second shank of the second leg of the person.

17. The method of claim 16, further including performing the steps of monitoring, determining, comparing, and identifying for the first leg and the second leg during the stride, utilizing shank angle and acceleration measurements from the first IMU and the second IMU.

18. The method of claim 17, wherein the steps of measuring, monitoring, determining, comparing, and identifying are performed for the first leg independent of the measurements from the second IMU on the second shank.

19. The method of claim 1, further comprising alerting the person when an overstride is identified.

20. A method for detecting overstride, the method comprising:
    measuring, using an inertial measurement unit (IMU) affixed to a shank of a person, an angle of the shank during a stride;
    monitoring, using a microprocessor, the shank angle measurements to identify a peak angle of the shank during the stride;
    comparing, using the microprocessor, the peak shank angle for the stride to a threshold shank angle; and
    identifying, using the microprocessor, an overstride of the corresponding leg if the peak shank angle exceeds the threshold shank angle.

21. The method of claim 20, wherein the IMU is positioned on a front or a side of the shank.

22. The method of claim 20, wherein the IMU is affixed to the shank using an anchoring member.

23. The method of claim 22, wherein an inner surface of the anchoring member includes an anti-slip material for frictionally engaging the shank.

24. The method of claim 23, wherein the anti-slip material is patterned to allow for heat transfer and sweat wicking through corresponding portions of the anchoring member.

25. The method of claim 22, wherein the anchoring member includes at least one of a compression sleeve and a substantially longitudinally inextensible sock.

26. The method of claim 20, wherein in the step of measuring, the shank angle is measured in a sagittal plane.

27. The method of claim 26, wherein in the step of monitoring, the peak shank angle is identified as the foremost shank angle in the forward direction of the stride.

28. The method of claim 20, wherein the threshold shank angle corresponds with a vertical direction of the sagittal plane.

29. The method of claim 20, wherein the threshold shank angle is approximately zero degrees in a coordinate system in which zero degrees corresponds with a vertical direction of the sagittal plane, positive angles correspond with a forward direction of the stride, and negative angles correspond with a rearward direction of the stride.

30. The method of claim 29, wherein in the step of identifying, an overstride occurs if the peak shank angle is positive.

31. The method of claim 1, wherein the threshold shank angle corresponds with an angle of the IMU affixed to the shank when the person is standing upright in a stationary position.

32. The method of claim 31, further including the step of determining the threshold shank angle during a calibration routine prior to the stride.

33. The method of claim 20, wherein in the step of identifying, the processor identifies an overstride of the corresponding leg utilizing measurements from only the IMU affixed to the shank of the corresponding leg.

34. The method of claim 20, wherein the step of measuring is performed for a first leg and a second leg of the person, using a first IMU affixed to a first shank of the first leg of a person, and a second IMU affixed to a second shank of the second leg of the person.

35. The method of claim 34, further including performing the steps of monitoring, comparing, and identifying for the first leg and the second leg during the stride, utilizing shank angle measurements from the first IMU and the second IMU.

36. The method of claim 35, wherein the steps of measuring, monitoring, comparing, and identifying are performed for the first leg independent of the measurements from the second IMU on the second shank.

37. The method of claim 20, further comprising alerting the person when an overstride is identified.

* * * * *

UNITED STATES PATENT AND TRADEMARK OFFICE
CERTIFICATE OF CORRECTION

PATENT NO. : 10,115,319 B2
APPLICATION NO. : 15/081072
DATED : October 30, 2018
INVENTOR(S) : Conor J. Walsh et al.

It is certified that error appears in the above-identified patent and that said Letters Patent is hereby corrected as shown below:

In the Specification

At Column 1, Line 14, please replace "None." with the following paragraph:
This invention was made with government support under W911NF-14-C-0051 and W911QX-12-C-0084 awarded by the U.S. Army. The government has certain rights in the invention.

Signed and Sealed this
Eighteenth Day of February, 2020

Andrei Iancu
*Director of the United States Patent and Trademark Office*